US006991777B2

(12) United States Patent
Driehuys et al.

(10) Patent No.: US 6,991,777 B2
(45) Date of Patent: Jan. 31, 2006

(54) METHODS FOR IN VIVO EVALUATION OF PHYSIOLOGICAL CONDITIONS AND/OR ORGAN OR SYSTEM FUNCTION INCLUDING METHODS TO EVALUATE CARDIOPULMONARY DISORDERS SUCH AS CHRONIC HEART FAILURE USING POLARIZED 129 XE

(75) Inventors: Bastiaan Driehuys, Chapel Hill, NC (US); Margaret Hall, Little Kingshill (GB); Claudio Marelli, Amersham (GB)

(73) Assignee: Medi-Physics, Inc., Princeton, NJ (US)

( * ) Notice: Subject to any disclaimer, the term of this patent is extended or adjusted under 35 U.S.C. 154(b) by 75 days.

(21) Appl. No.: 10/236,156

(22) Filed: Sep. 6, 2002

(65) Prior Publication Data

US 2003/0064023 A1    Apr. 3, 2003

Related U.S. Application Data

(60) Provisional application No. 60/323,775, filed on Sep. 20, 2001.

(51) Int. Cl.
*A61K 49/00* (2006.01)
(52) U.S. Cl. ...................... 424/9.1; 424/1.11; 424/1.65; 424/1.81
(58) Field of Classification Search ................ 424/1.11, 424/1.65, 9.1, 9.3, 9.32, 9.36, 1.81
See application file for complete search history.

(56) References Cited

U.S. PATENT DOCUMENTS

| | | | |
|---|---|---|---|
| 5,190,744 A | 3/1993 | Rocklage et al. | |
| 5,352,979 A | 10/1994 | Conturo | |
| 5,494,655 A | 2/1996 | Rocklage et al. | |
| 5,509,412 A | 4/1996 | Bahn | |
| 5,522,390 A | 6/1996 | Tuithof et al. | |
| 5,545,396 A | 8/1996 | Albert et al. | |
| 5,833,947 A | 11/1998 | Rocklage et al. | |

FOREIGN PATENT DOCUMENTS

WO    WO 99/47940    9/1999

OTHER PUBLICATIONS

Webber et al., Measuring Diffusion of Xenon in solution with hyperpolarized 129Xe NMR, 296 Chemical Physics Letters, p. 391-396, (Nov. 6, 1998).
Hou et al., Optimization of Fast Acquisition Methods for Whole-Brain Relative Cerebral Blood Volume (rCBV) Mapping with Susceptibility Contrast Agents, 9 J. Magnetic Resonance Imaging 233 (1999).
Simonsen et al., CBF and CBV Measurements by USPIO Bolus Tracking: Reproducibility and Comparison with Gd-Based Values, 9 J. Magnetic Resonance Imaging 342 (1999).
Swanson, et al., Distribution and Dynamics of Laswer-Polarized 129Xe Magnetization In Vivo, Magnetic Resonance in Medicine, pp. 1137-1145 (1999).
Lassen, Cerebral Transit of an Intravascular Tracer may Allow Measurement of regional Blood Volume but not Regional Blood Flow, 4 J. Cereb. Blood Flow and Metab. 633 (1984).
Belliveau et al., Functional Cerebral Imaging by Susceptibility-Contrast NMR, 14 Magnetic Resonance in Medicine 14 538 (1990).
Detre et al., Measurement of Regional Cerebral Blood Flow in Cat Brain Using Intracarotid 2H20 and 2H NMR Imaging, 14 Magnetic Resonance in Medicine 389 (1990).
Frank et al., Dynamic Dysprosium-DTPA-BMA Enhanced MRI of the Occipital Cortex; Functional Imaging in Visually Impaired Monkeys by PET and MRI (Abstract), Ninth Annual Scientific Meeting and Exhibition of the Society of Magnetic Resonance In Medicine (Aug. 18-24, 1990).
Ruppert et al., NMR of Hyperpolarized 129Xe in the Canine Chest: Spectral Dynamics During a Breath-Hold, 13 NMR in Biomedicine, p. 220-228 (2000).
Le Bihan, Magnetic Resonance Imaging of Perfusion, 14 Magnetic Resonance in Medicine 283 (1990).
Rosen et al., Perfusion Imaging by Nuclear Magnetic Resonance, 5 Magnetic Resonance Quarterly 263 (1989).
Maier T., et.al. Detection of Dissolved Hyperpolarized / sup 129/Xe in Human Brain, Proceedings of the International Society For Magnetic Resonance in Medicine, Sixth Scientifice Meeting and Exhibition, vol. 3, Apr. 1998, p. 1907.
Swanson S D, et.al. Brain MRI with Laser P larized 129 Xe, Magnetic Resonance in Medicine, Academic Press, Duluth, MN, US vol. 38, No. 5, Nov. 1, 1997, pp. 695-698.
Gao J-H, et.al. "Magnetization and Diffusion Effects in NMR Imaging of Hyperpolarized Substances" Magnetic Resonance in Medicine, Academic Press, Duluth, MN, US vol. 37, No. 1, 1997 pp. 153-158.
Peled S, et.al, "Determinants of tissue delivery for /sup129/Xe Magnetic Resonance in Humans" Magnetic Resonance in Medicine, Sep. 1996, Willimas & Wilkins, USA, vol. 36, No. 3, pp. 340-344.

*Primary Examiner*—Dameron L. Jones
(74) *Attorney, Agent, or Firm*—Robert F. Chisholm

(57) ABSTRACT

In certain embodiments, methods of the present invention obtain NMR spectroscopy signal data that corresponds to the behavior of the polarized $^{129}$Xe at a selected site(s) in selected environments in vivo. The gas exchange signal data can be used to evaluate: (a) the thickness of a barrier, such as a membrane, lining, wall or width of a lumen; (b) the operational condition or function of a membrane, body system or portion thereof; (c) cerebral perfusion; and/or (c) the efficacy of a therapeutic treatment used to treat a diagnosed disorder, disease, or condition. Thus, the present invention provides methods for screening and/or diagnosing a disorder or disease, and/or methods for monitoring the efficacy of therapeutics administered to subject to treat a disorder or disease.

6 Claims, 14 Drawing Sheets

METHODS FOR IN VIVO EVALUATION OF PHYSIOLOGICAL CONDITIONS AND/OR ORGAN OR SYSTEM FUNCTION INCLUDING METHODS TO EVALUATE CARDIOPULMONARY DISORDERS SUCH AS CHRONIC HEART FAILURE USING POLARIZED 129 XE

This application claims benefit of 60/323,775 filed Sep. 20, 2001, the entire disclosure which is herein incorporated by reference.

FIELD OF THE INVENTION

The present invention relates to magnetic resonance imaging ("MRI") and MR spectroscopy using hyperpolarized noble gases. More particularly, the present invention relates to techniques to assess certain physiology, conditions, and/or functions of organs or body systems in vivo using polarized noble gases.

BACKGROUND OF THE INVENTION

Conventionally, MRI has been used to produce images by exciting the nuclei of hydrogen molecules (present in water protons) in the human body. However, it has recently been discovered that polarized noble gases can produce improved images of certain areas and regions of the body that have heretofore produced less than satisfactory images in this modality. Polarized Helium 3 ("$^3$He") and Xenon-129 ("$^{129}$Xe") have been found to be particularly suited for this purpose. See U.S. Pat. No. 5,545,396 to Albert et al., entitled "Magnetic Resonance Imaging Using Hyperpolarized Noble Gases", the disclosure of which is hereby incorporated by reference herein as if recited in full herein.

In order to obtain sufficient quantities of the polarized gases necessary for imaging, hyperpolarizers are used to produce and accumulate polarized noble gases. Hyperpolarizers artificially enhance the polarization of certain noble gas nuclei (such as $^{129}$Xe or $^3$He) over the natural or equilibrium levels, i.e., the Boltzmann polarization. Such an increase is desirable because it enhances and increases the Magnetic Resonance Imaging ("MRI") signal intensity, thereby potentially allowing physicians to obtain better images of many tissues and organs in the body.

Generally stated, in order to produce the hyperpolarized gas, the hyperpolarizer is configured such that the noble gas is blended with optically pumped alkali metal vapors such as rubidium ("Rb"). These optically pumped metal vapors collide with the nuclei of the noble gas and hyperpolarize the noble gas through a phenomenon known as "spin-exchange". The "optical pumping" of the alkali metal vapor is produced by irradiating the alkali-metal vapor with circularly polarized light (typically provided by lasers) at the wavelength of the first principal resonance for the alkali metal (e.g., 795 nm for Rb). Generally described, the ground state atoms become excited, then subsequently decay back to the ground state. In the presence of non-zero nuclear spin noble gases, the alkali-metal vapor atoms can collide with the noble gas atoms in a manner in which the polarization of the valence electrons is transferred to the noble-gas nuclei through a mutual spin flip "spin-exchange".

After the spin-exchange has been completed, the hyperpolarized gas is separated from the alkali metal prior to introduction into a patient.

Conventionally, gas-phase imaging has been possible using both $^3$He and $^{129}$Xe, and has been particularly useful in producing ventilation-driven images of the lungs, a region where proton images have produced signal voids. However, in contrast to gas phase imaging, dissolved phase imaging has proven to be problematic. Dissolved phase imaging uses the solubility characteristic of $^{129}$Xe in blood and lipid rich tissue. The gas phase is thus absorbed or "dissolved" into surrounding tissue or blood vessels and may allow perfusion imaging of the brain, lung, or other regions. Such images can potentially allow for the performance of non-invasive studies of the pulmonary vasculature to detect emboli and other circulatory system problems. Unfortunately, once the polarized gas has been dissolved (such as into the blood vessels), it has proven difficult to generate clinically useful images using the dissolved phase gas.

For example, MRI images using gas-space-imaging techniques have been generated using hyperpolarized $^{129}$Xe gas. See Mugler III et al., *MR Imaging and Spectroscopy Using Hyperpolarized $^{129}$Xe gas: Preliminary Human Results*, 37 Magnetic Resonance in Medicine, pp. 809–815 (1997). While good correlation is seen between the gas-space signal in the xenon images and the gas-space signal void in the proton images, the spectra associated with the dissolved phase signal components were significantly lower than the gas-phase signal.

There remains a need to provide clinically useful methods for using polarized gas to perform in vivo evaluations of the body.

SUMMARY OF THE INVENTION

In certain embodiments, methods of the present invention obtain dynamic NMR spectroscopy signal data that corresponds to the behavior of polarized $^{129}$Xe at a selected site(s) or environment in vivo. The signal data can be used to evaluate: (a) the physiology (tissue volume or thickness/width) of a membrane, organ, tissue, or other physiological structure or environment; (b) the operational condition or function of a membrane, body system, or portion thereof; (c) cerebral perfusion; and/or (c) the efficacy of a therapeutic treatment used to treat a diagnosed disorder, disease, or condition. Thus, the present invention provides methods for screening and/or diagnosing a disorder or disease, and/or methods for monitoring the efficacy of therapeutics administered to subject to treat a disorder or disease.

Particular embodiments of the present invention use $^{129}$Xe as a tracer for oxygen. A curve can be best-fit to the dynamic data to represent the behavior of the polarized $^{129}$Xe at selected chemical shifts or frequencies. The curve can have various characterizing parameters including: an associated time constant, peak amplitude, amplitude at the time constant, slope of linear portions, and the like. These characterizing parameters can be used to evaluate the target of interest.

For example, the curve can illustrate the transit time of polarized $^{129}$Xe in a target in the body. Delayed (longer) transit times may represent thicker tissue, or poor perfusion to help evaluate whether the subject may be hypoxic (in one or more areas such as in the pulmonary blood, the cardiac region, or in the brain). The polarized $^{129}$Xe can be used to determine whether low oxygen saturation is the result of poor ventilation, poor perfusion, and/or poor gas diffusing capacity across tissue or membranes. Such an analysis can be used to monitor therapeutic efficacy or disease progression.

In certain embodiments, a dynamic data set of the signal strength of the $^{129}$Xe in selected tissue or environments over time can be generated and evaluated. Such information can be used in various manners such as to assess perfusion uptake, or the function of selected membranes, linings, and biosystems. The dynamic data set corresponds to the accrual, build up, or increase in signal strength over time of $^{129}$Xe at one or more chemical shift frequencies or ppm.

Particular embodiments of the present invention are directed to minimally or non-invasive in vivo methods for evaluating the thickness or width of a physiological barrier such as a membrane, lining, lumen, channel, or wall in a subject using polarized $^{129}$Xe. The method includes: (a) delivering polarized $^{129}$Xe gas in vivo to a subject having a first environment, a physiological barrier having a thickness, and a second environment opposing the first environment such that the polarized $^{129}$Xe travels serially through the first environment, the barrier, and into the second environment, wherein the polarized $^{129}$Xe has an associated different NMR signal chemical shift frequency in the first and second environments and the barrier; (b) destroying the polarization of the $^{129}$Xe in the barrier and the second environment; (c) obtaining an NMR spectroscopic signal of the polarized gas in the subject at the second chemical shift to generate at least one dynamic data set of the NMR spectroscopic signal strength values over time representative of the behavior of the polarized $^{129}$Xe as it crosses the barrier and enters the second environment; (d) evaluating the polarized gas transit time of the polarized gas, the gas transit time corresponding to the time it takes the polarized gas to travel across the barrier and then enter the second environment, based on data provided by said obtaining step; and (e) determining the thickness or width of the barrier based on data provided by the calculating step.

The method may further include (a) generating a signal strength versus time curve to fit the dynamic data; (b) identifying a time constant of the curve; and (c) evaluating the amplitude of the signal strength at a time along the curve corresponding to the time constant.

In other embodiments, the operation or function of the membrane can be evaluated without determining the thickness of the membrane. In particular embodiments, the method can be used to measure membranes having a thickness in the range of about 1 micron to about 100 microns.

Another embodiment is directed to in vivo methods for evaluating the blood brain barrier in a subject. The method comprises: (a) delivering polarized $^{129}$Xe in vivo to a subject such that it diffuses into the blood stream, across the blood brain membrane, and is taken up in tissue in the brain across the membrane, the polarized gas in the blood, membrane, and brain tissue having distinct corresponding polarized gas NMR chemical shift signal frequencies; (b) destroying the polarization of the polarized $^{129}$Xe in at least the brain tissue; (c) obtaining an NMR spectroscopic signal of the polarized gas in the subject over time at the brain tissue chemical shift frequency to generate at least one dynamic data set of the NMR spectroscopic signal strength values over time; (d) evaluating the dynamic data; and (e) assessing the blood brain barrier based on data provided by the obtaining and evaluating steps.

Other embodiments of the present invention are directed at methods for monitoring gas exchange dynamics of $^{129}$Xe at or across the blood brain barrier to evaluate inflammatory disorders of the brain such as meningitis, encephalitis, and the like and/or to provide methods that can distinguish between certain disorders such as between meningitis and cerebritis by analyzing the gas exchange reaction at the blood barrier membrane. Still other embodiments are directed to measurement of organ perfusion by monitoring xenon transport in, to, or through, that organ.

Still other embodiments are directed to methods of obtaining cerebral perfusion information. The method comprises: (a) administering polarized $^{129}$Xe to a subject in vivo; (b) concurrently obtaining a plurality dynamic data sets of NMR spectrographic signal strength of the polarized $^{129}$Xe in a compartment of the brain of the subject representative of perfusion in the brain, each dynamic data set corresponds to a different chemical shift frequency; (c) repeating step (b) for a plurality of different compartments across the brain; and (d) generating at least one perfusion image of the brain based on the data provided by the obtaining steps, wherein the image comprises a plurality of voxels associated therewith, and wherein each voxel corresponds to a measure of perfusion in the associated compartment in the brain.

Other embodiments are directed to in vivo methods for evaluating at least one of the thickness of adequacy of function of a membrane or lining, comprising: (a) delivering polarized $^{129}$Xe in vivo to a subject such that the polarized $^{129}$Xe moves across the membrane or wall, the polarized gas in the membrane or wall having a corresponding polarized gas NMR chemical shift signal frequency; (b) obtaining an NMR spectroscopic signal of the polarized gas in the subject over time at the chemical shift frequency to generate at least one dynamic data set of the NMR spectroscopic signal strength values over time; and (c) evaluating at least one of (1) the adequacy of function of the membrane or lining and (2) the thickness of the membrane or lining based on the data provided by said obtaining step.

Another embodiment of the present invention is directed to a computer program product for evaluating bioactivity, physiology, and/or perfusion in vivo. The computer program product includes computer readable storage medium having computer readable program code embodied in the medium, the computer-readable program code comprises: (a) computer readable program code that obtains an NMR spectroscopic signal of polarized $^{129}$Xe in the subject over time at at least one selected chemical shift frequency to generate at least one dynamic data set of the NMR spectroscopic signal strength over time; and (b) computer readable program code that analyzes the dynamic data set for at least one of: (a) quantifying the thickness of a physiologic barrier such as a tissue, membrane, or lining of interest (b) quantifying the width of a lumen or channel; (c) evaluating the adequacy of physiologic function of certain biosystems or membranes; (d) identify disruptions or compromised integrity of physiological barriers, structures, lumens, or channels and/or to identify disorders associated therewith; and (e) to provide a cerebral perfusion map of the brain based on a concurrent acquisition of dynamic data at multiple chemical shifts associated with the brain across a plurality of compartments of the brain.

Further, the instant invention can use spectroscopic or MRI imaging techniques to obtain signal data corresponding to a quantity of dissolved polarized $^{129}$Xe before and after a physiologically active substance is administered to a human or animal body to evaluate the efficacy of the drug treatment.

As will be appreciated by those of skill in the art in light of the present disclosure, embodiments of the present invention may include methods, systems and/or computer program products. The foregoing and other objects and aspects of the present invention are explained in detail herein.

DETAILED DESCRIPTION OF EMBODIMENTS OF THE INVENTION

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, layers, regions or features may be exaggerated for clarity. Broken lines in the figures represent optional features or operations.

As known to those of skill in the art, polarized gases are collected, frozen, thawed, and used in MRI and NMR spectroscopy applications. For ease of description, the term "frozen polarized gas" means that the polarized gas has been frozen into a solid state. The term "liquid polarized gas" means that the polarized gas has been or is being liquefied into a liquid state. Although each term includes the word "gas", this word is used to name and descriptively track the gas that is produced via a hyperpolarizer to obtain a polarized "gas" product. Thus, as used herein, the term "gas" has been used in certain instances to descriptively indicate a hyperpolarized noble gas product and may be used with modifiers such as solid, frozen, dissolved, and liquid to describe the state or phase of that product. Also, for certain embodiments, the hyperpolarized gas is processed such that it is a pharmaceutical grade product suitable for in vivo delivery to a human subject. In particular embodiments, the $^{129}$Xe gas product is formulated to have less than about 10 ppb (parts per billion) alkali metal therein, and can have less than about 1 ppb.

Various techniques have been employed to accumulate and capture polarized gases. For example, U.S. Pat. No. 5,642,625 to Cates et al. describes a high volume hyperpolarizer for spin-polarized noble gas, and U.S. Pat. No. 5,809,801 to Cates et al. describes a cryogenic accumulator for spin-polarized $^{129}$Xe. U.S. Pat. No. 6,079,213 to Driehuys et al., entitled "Methods of Collecting, Thawing, and Extending the Useful Life of Polarized Gases and Associated Apparatus", describes an improved accumulator and collection and thaw methods. The disclosures of these documents are hereby incorporated by reference as if recited in full herein.

As used herein, the terms "hyperpolarize," "polarize," and the like are used interchangeably and mean to artificially enhance the polarization of certain noble gas nuclei over the natural or equilibrium levels. Such an increase is desirable because it allows stronger imaging signals corresponding to better MRI images and spectroscopy signals of the gas in the body. As is known by those of skill in the art, hyperpolarization can be induced by spin-exchange with an optically pumped alkali-metal vapor or alternatively by metastability exchange. See Albert et al., U.S. Pat. No. 5,545,396.

Figure 1:
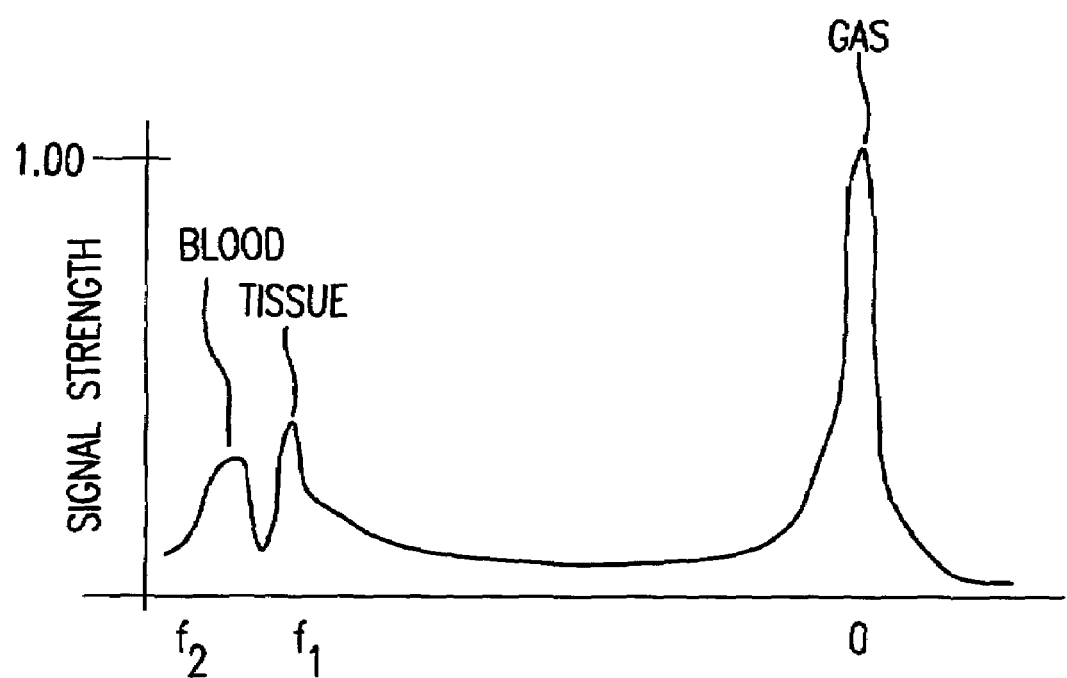
FIG. 1 is a graph of $^{129}$Xe spectra showing the spectral signal of different chemical shifts of polarized xenon in blood and tissue.

Referring now to FIG. 1, NMR signal strength spectrum data (obtained in vivo) of polarized $^{129}$Xe in the body of a subject is illustrated. The dissolved-phase spectra are shown on the left side of the figure (indicated by peaks at $f_1$ and $f_2$). The gas-phase spectra (on the right side of the figure at "0") have a larger signal relative to the spectra of the $^{129}$Xe dissolved in blood or tissue. When a quantity of polarized $^{129}$Xe is inhaled into the lungs, a small fraction of this gas (roughly about 0.3% per/second) transits into the pulmonary blood. It is known that polarized $^{129}$Xe in the lung exhibits three distinct NMR resonances: 0 parts per million ("ppm") is associated with gaseous $^{129}$Xe, 197 ppm is associated with $^{129}$Xe dissolved in lung tissue ($f_1$), and 212 ppm is associated with $^{129}$Xe dissolved in blood ($f_2$). Each of the signal strengths at these resonances (or others) can be tracked as a function of time.

Table 1 listed hereinbelow illustrates examples of NMR resonances of additional bio-substances. Signal strength for the selected resonances can be tracked as a function of time with at least about millisecond resolution. Other peaks at other locations, environments, tissues or membranes in the body may be selected in other embodiments.

Generally stated, the present invention monitors the behavior of the polarized $^{129}$Xe in the body by obtaining the signal strength over time between or at certain regions of the body to ascertain certain physiologic, performance, or systemic function information. For example, referring now to FIG. 2A, polarized $^{129}$Xe is administered to a subject such that it is present in proximate regions, i.e., region 1 (identified by the number 1), and region 2 (identified by the number 2). As shown, in certain embodiments, region 1 and region 2 can be separated by a barrier 10 such as a wall, membrane, tissue or other structure. As shown in FIG. 2B, the polarized gas in region 1 has a chemical shift which is distinct from the polarized gas into region 2. In certain embodiments, the barrier 10 can also have a signal with its own chemical shift.

Figure 2A:
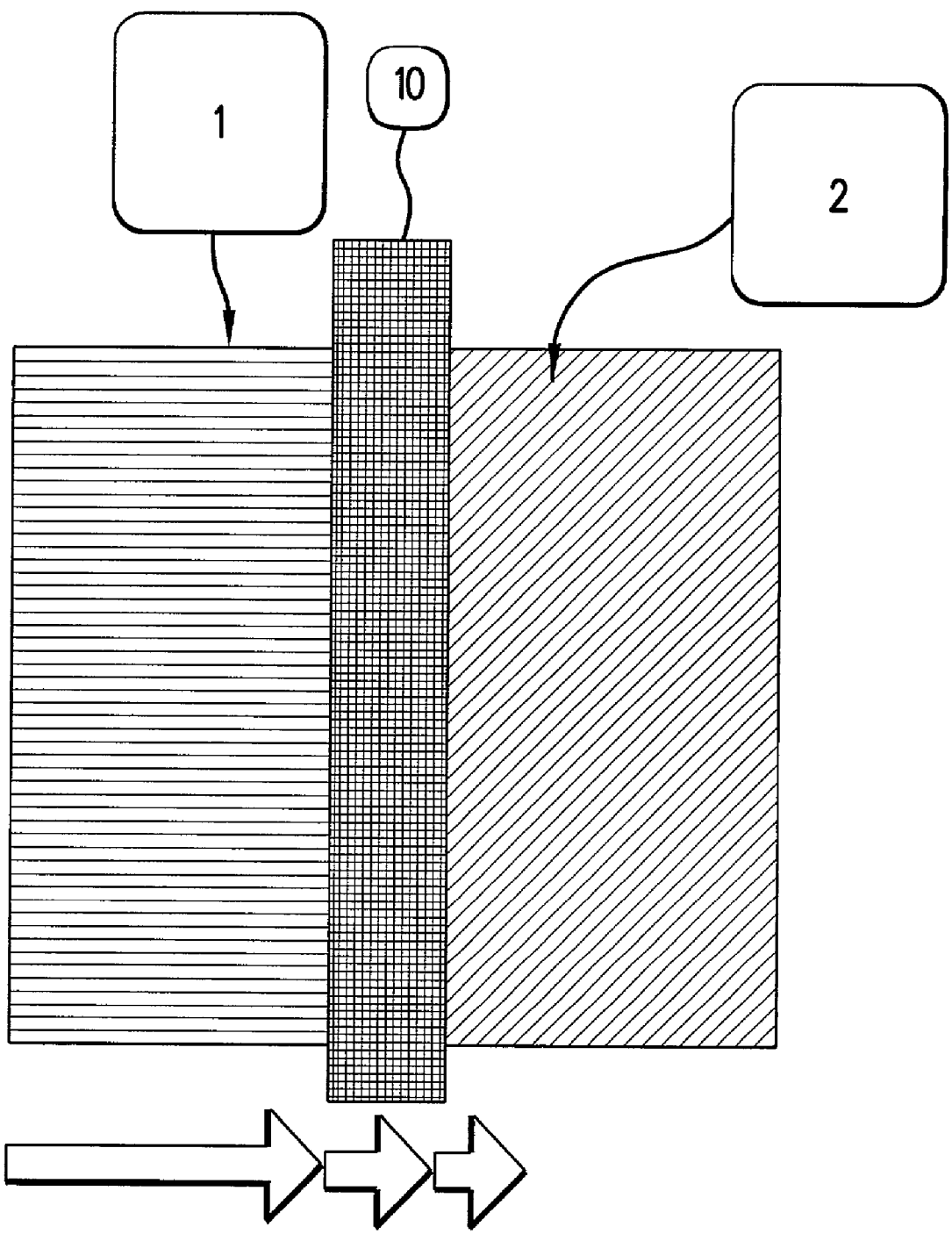
FIG. 2A is a schematic illustration of polarized gas distributed into two proximate regions in the body according to embodiments of the present invention.
Figure 2B:
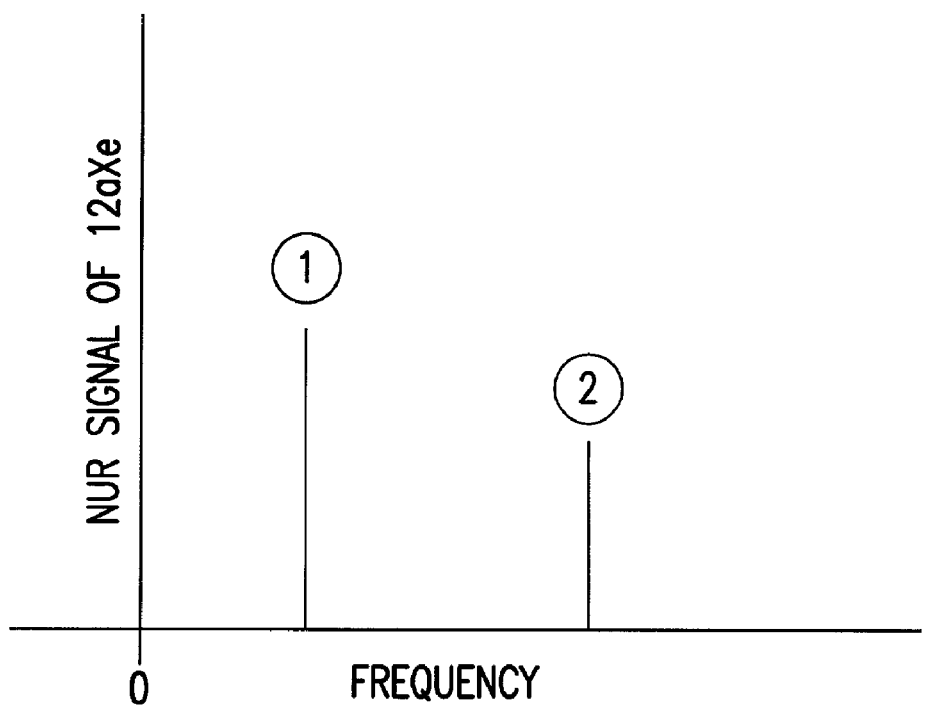
FIG. 2B is a simulated graph illustrating the chemical shifts associated with the two regions shown in FIG. 2A.
Figure 2C:
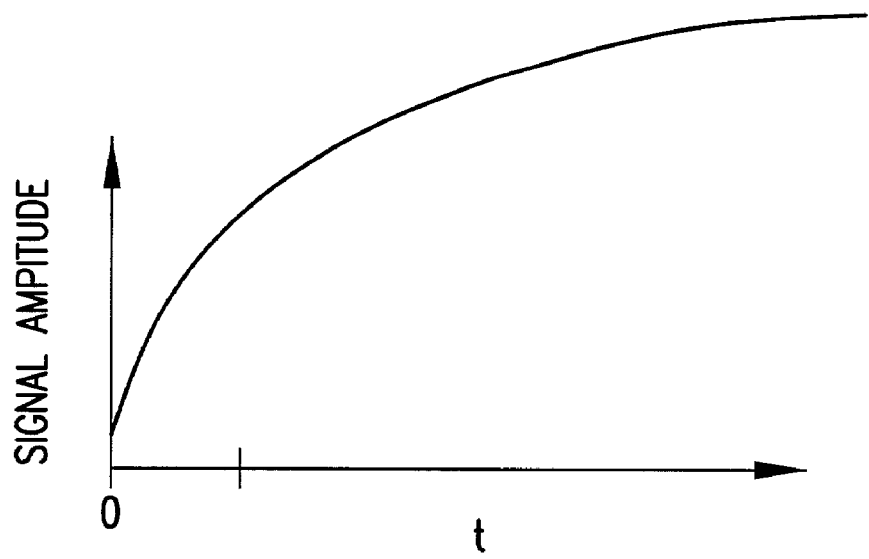
FIG. 2C is a graph of signal strength as a function of time of the polarized gas in region two of FIG. 2A according to embodiments of the present invention.

In operation, as shown by the arrows in FIG. 2A, the polarized gas in region 1 (either in gaseous or dissolved state) can travel or diffuse to, and hence supply, the polarized gas in region 2. As shown in FIG. 2C, the build-up of signal of the polarized gas in region 2 can be dynamically monitored. The transit time can be described as the time it takes for the polarized gas to cross the barrier 10 in sufficient quantities or amounts to yield a detectable signal and/or to approach a substantially steady state condition in signal strength therefrom. In particular embodiments, a curve or line can be statistically "best-fit" to the dynamic data or signal strength over time. The line or curve will have an associated time constant ($\tau$) which can be used to represent the transit time of the gas through the barrier 10. The curve or line will have other characterizing parameters which are measurable or representative of physiologic condition, structure, or function, as will be discussed more below.

In operation, the polarization, and hence the signal, in region 2 (and the membrane or barrier 10) can be destroyed (such as by transmitting a large RF excitation signal to that region) and then the signal in region 2 can be monitored as the signal strength of the chemical shift spectra of the polarized gas entering region 2 rebuilds from the ongoing supply of polarized gas delivered thereto during the analysis period.

FIG. 2C illustrates that the dynamic data can be generated with sufficient resolution to be able to measure uptake with sufficient resolution to obtain data points of signal strength over time to define a slope or line shape corresponding to the dynamic behavior of the polarized $^{129}$Xe in the tissue, region, or barrier. For example, the dynamic data can be obtained so as to provide signal strength data for a time which is at least twice the time constant to allow for a sufficient number of data points to render a representative line or curve. The time constants typically range from about 0.25 ms to about 2.5 seconds.

In operation, in certain particular embodiments, a dynamic data set of NMR spectroscopic blood signal strength of polarized $^{129}$Xe in an environment of interest (such as blood) over time at at least one chemical peak or shift of interest can be obtained and evaluated to assess certain physiological parameters, structures, or function of the structure or body systems or portions thereof (nervous system, circulatory, respiratory, or cerebral). The parameters can include, but are not limited to, one or more of perfusion uptake, the function or integrity of a physiologic structure such as a membrane, lining, or wall, and/or the thickness of the barrier or structure, including the membrane, lining, wall or the width of a lumen (such as a capillary or other lumen), red blood cell, or a body cavity. Characterizing parameters provided by the dynamic data include the time it takes the polarized gas to travel through the barrier or a selected tissue or environment (i.e., the transit time which can be represented by a calculated time constant as noted above), the oxygen saturation level or measure of ventilated blood volume (as a measure of shunt) in the patient. The dynamic data set corresponds to the accrual, build up, or increase in signal strength of a particular signal or signals with an associated chemical shift (such as in the pulmonary blood, the cerebral blood, or alveolar tissue), over time.

Figure 3A:
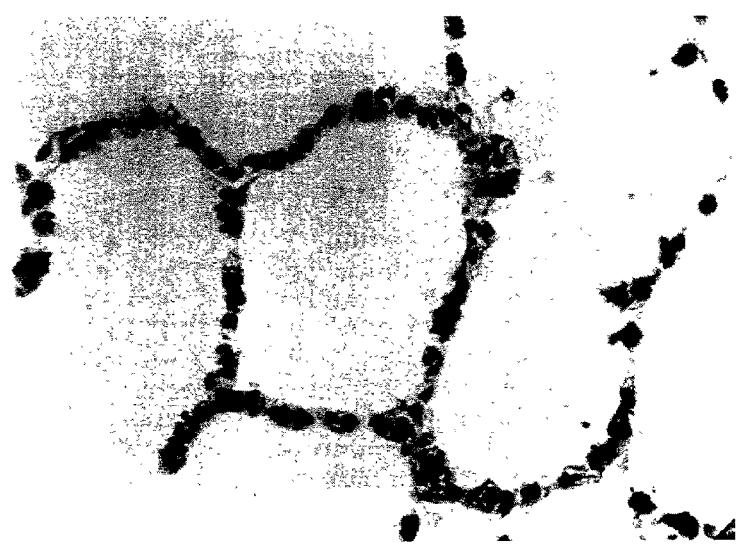
FIG. 3A is a micrograph of lung tissue and alveoli structure.
Figure 3B:
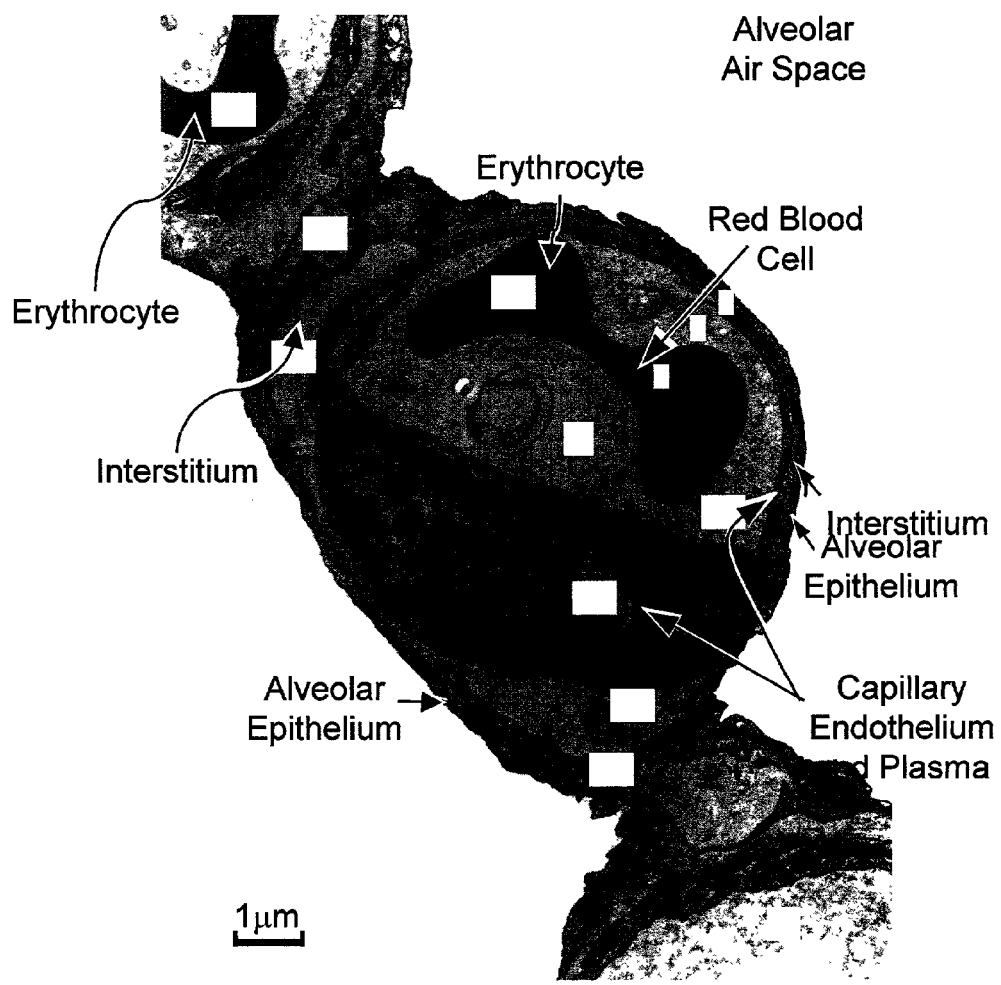
FIG. 3B is an enlarged micrograph of alveolar structure illustrating the capillary and alveolar air space and red blood cells.

FIG. 3A is a micrograph of lung tissue or alveolar structure. FIG. 3B is enlarged (20×) compared to the scale shown in FIG. 3A and illustrates alveolar structure including the alveolar epithelium (Ep), the interstitium (Ei), the capillary endothelium (En), a capillary (C) and red blood cell (R) and alveolar air space (A). The present invention provides methods for evaluating gas transit behavior across lung tissue, and/or across the alveolar-capillary membrane into the pulmonary blood. In certain embodiments, this information can be used to evaluate chronic heart failure ("CHF") because CHF typically disturbs the alveolar-capillary membrane and increases the resistance to polarized gas transfer as the gas attempts to travel toward the pulmonary blood (into the red blood cells). Elevation of the capillary pressure can increase the capillary permeability to water and ions and disrupt local regulatory mechanisms for gas exchange, leading to thickening of the alveolar-capillary interstitium, and/or to a decrease in membrane conductance and subsequent impairment of diffusion capacity. Monitoring of the transit time and/or behavior of $^{129}$Xe acting as a tracer across a membrane in resting conditions and during (incremental) actual or simulated exercise (and/or after administration of a pharmaceutical product or therapeutic agent) can be performed so as to measure the function of the alveolar-capillary membrane. Other physiology or structures, membranes, or other barriers and associated peaks and regions can be monitored for other conditions as noted above.

Figure 5A:
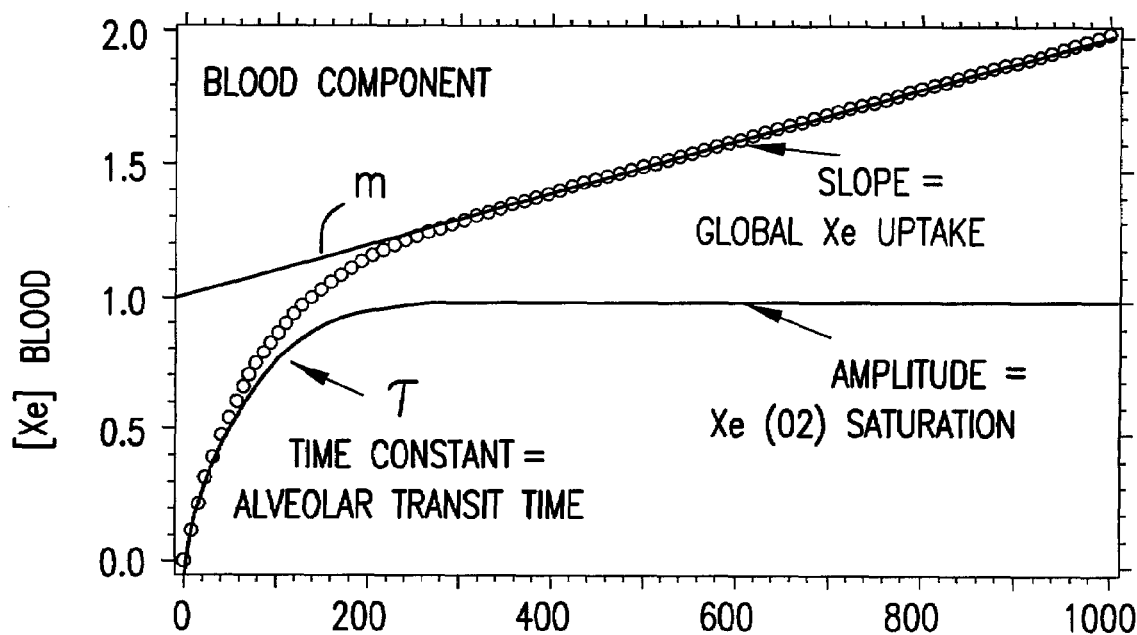
FIG. 5A is a simulated graph of the signal of the $^{129}$Xe blood component over time according to embodiments of the present invention. The signal amplitude in blood is shown as one of the peaks of interest in FIG. 1.
Figure 5B:
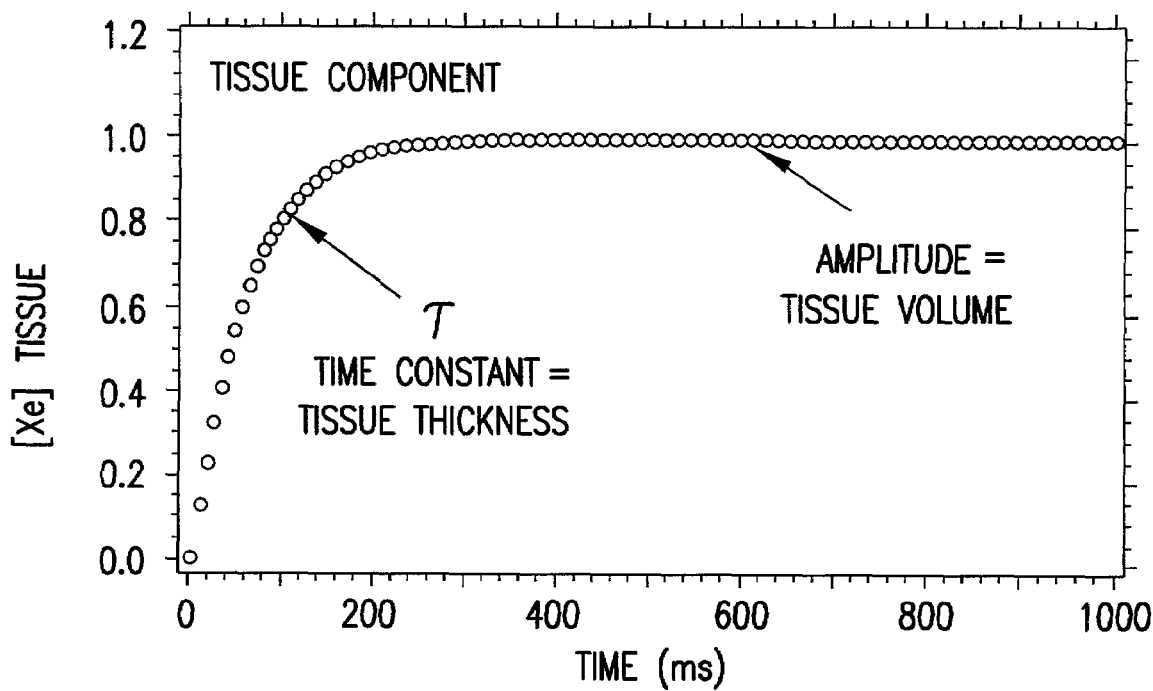
FIG. 5B is a simulated graph of the signal of the $^{129}$Xe tissue component over time according to embodiments of the present invention. The signal amplitude in tissue is shown as one of the peaks of interest in FIG. 1.

FIG. 5A illustrates the signal strength of the $^{129}$Xe in blood ($f_2$) over time and FIG. 5B illustrates the signal strength of the $^{129}$Xe in tissue ($f_1$) over time. To obtain the curve or line shape representing the gas exchange or diffusion process in the body at a selected frequency or shift of interest, a series of increasingly longer pulses are transmitted to generate the response signal. A plurality of different dynamic data sets, each at different discrete frequencies or chemical shifts can be obtained concurrently.

To generate the dynamic data set of the $^{129}$Xe in the body, polarized $^{129}$Xe is administered to the subject or patient. Then the polarization of the polarized $^{129}$Xe can be destroyed in a selected in vivo environment, structure, or physiology and then allowed to rebuild. For example, gaseous polarized $^{129}$Xe can be inhaled into the lungs and then the $^{129}$Xe can diffuse to, and hence supply, the polarized $^{129}$Xe into the membrane (as it diffuses serially across Ep, Ei, and then En) and into the capillary and the pulmonary blood.

Figure 4:
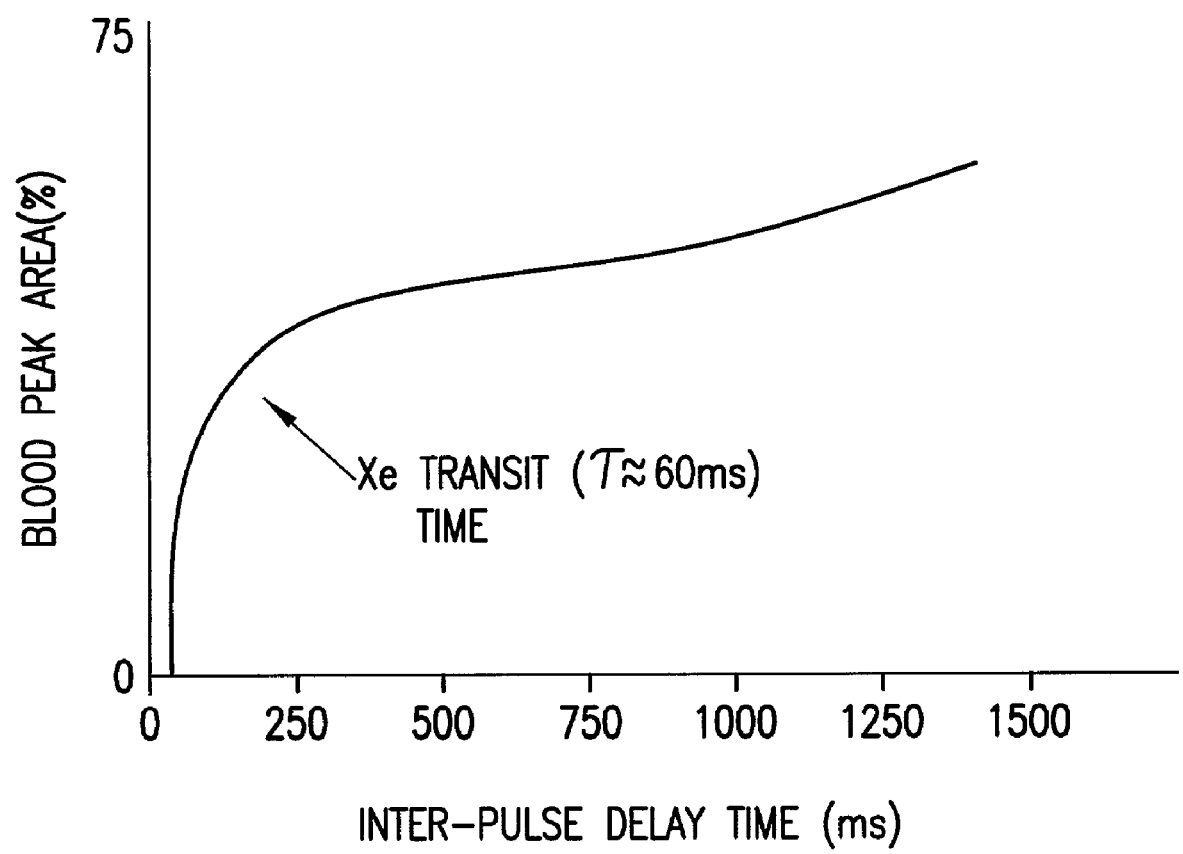
FIG. 4 is a graph illustrating the uptake of polarized $^{129}$Xe in blood over time according to embodiments of the present invention.

As shown in FIG. 4, the build up of signal of the polarized $^{129}$Xe in a selected environment can be dynamically monitored to determine a time constant "$\tau$" associated with transit time of the polarized $^{129}$Xe as it diffuses across the environment of interest (such as a lining, wall, or membrane).

In operation, in certain embodiments, to measure the time constant and/or obtain dynamic data, the polarization, and hence the signal, in the barrier (which, for the alveolar-capillary membrane, can include the alveolar epithelium, the interstitium, and the capillary endothelium) and in the proximate blood in the capillary/red blood cell(s) can be destroyed by transmitting a large angle RF excitation pulse thereto to define t=0 (defined as the time after the polarization is destroyed). Then NMR signal strength data of the polarized $^{129}$Xe is collected for a first time period. The signal strength of the chemical shift spectra of the polarized gas entering the blood increases over time as it rebuilds from "0" from the ongoing supply of polarized gas delivered from the lungs during the analysis period.

Then the polarization is destroyed again and a second data collection is commenced by transmitting a second excitation pulse that is initiated at a second time (delayed relative to the first excitation to obtain data associated with the polarized $^{129}$Xe at a period that is later in time from the first excitation), such as at t=40 ms. Thus, to generate the line or curve (at least electronically) associated with the dynamic data set, the polarization is destroyed a plurality of times and then a series of incrementally spaced excitation pulses are transmitted to generate a response curve which maps the $^{129}$Xe behavior in vivo with at least about millisecond resolution. Stated differently, the polarization is destroyed each time and then the response data is collected at successively longer times to collect the signal data at the desired times in the analysis period. The NMR data can be collected using decremented pulse intervals (starting with the longest interval and moving to the shortest) or other sequences as desired. The data can be collected and the response curve of the $^{129}$Xe can be generated using curve fit using statistical analysis techniques well known to those of skill in the art. Other peaks at other locations, environments, tissues or membranes in the body may be selected in other embodiments and similarly evaluated for function.

FIGS. 5A and 5B illustrate that the dynamic data can be generated with sufficient resolution to measure uptake with sufficient resolution to define a line shape corresponding to the uptake of the $^{129}$Xe. To obtain sufficient data points to generate the time constant "$\tau$", the signal data can be collected for times that are at least two times that of the time constant. Thus, for time constants of 60 ms, data can be collected for at least about 120 ms. In certain embodiments, the time constant "$\tau$" can be used to determine the thickness or width of the barrier.

Other embodiments of the invention assess or evaluate other conditions of other membranes or walls associated with lumens or natural body cavities that may be impaired in integrity or function. For example, the glomerular capillary membrane can be evaluated by administering polarized $^{129}$Xe to assess for any disruptions, apertures, permeability and flow rate across this membrane to give a quantitative assessment in health and disease. One result may be to record glomerular filtration rate and this could be given globally or for each individual kidney. This is useful in many clinical situations, e.g., measuring GFR prior to chemotherapy administration. In disorders such as the glomerulonephritidtis, the disease affects the structure and function of the membrane so the methods of the present invention can be used to monitor disease progression and effect of therapy. The disorders involved here may be acute and chronic renal failure, nephrotic syndrome, glomerulonephritis and other renal diseases. Similarly, the proximal or distal renal tubules may be evaluated using polarized $^{129}$Xe.

In still other embodiments, the function of the large and/or small bowel wall can be evaluated. A quantitative assessment of bowel membrane integrity and function may be useful in a variety of gastroenterological diseases. In other embodiments, the placental membrane may be evaluated. The polarized $^{129}$Xe may be administered to the mother via inhalation or injection proximate to the placental membrane itself. A minimally or non-invasive method of assessing placental integrity and function other using $^{129}$Xe can provide additional information over conventional techniques (such as to observe the consequences of poor function by measuring fetal growth). Such a method of giving quantitative placental function may be a useful clinical tool in obstetrics.

In alterative embodiments, the blood brain barrier can be evaluated so as to quantify or evaluate the integrity and function of this barrier or conditions associated therewith. The evaluation of the blood brain barrier can be to evaluate thickness or function or to assess for inflammatory disorders of the brain such as meningitis, encephalitis, and the like and/or to provide methods that can distinguish between certain disorders such as between meningitis and cerebritis by analyzing the gas exchange reaction at the blood barrier membrane. Other embodiments include assessing blood cell physiology or function defects or abnormalities (such as evaluating the presence or degree of sickle cell anemia).

As shown in FIG. 5A, in certain embodiments, after inhalation of hyperpolarized $^{129}$Xe, its uptake into a barrier, blood, or tissue can be measured as a function of time. The initial build-up rate (after the polarization is substantially destroyed in the membrane and the blood) of the xenon/blood or xenon/tissue signal is sensitive to barrier thickness. The spectroscopic signal of the xenon/blood or xenon/tissue can be used to quantify the thickness and/or the degree of edema or the function or thickness of the barrier associated with various conditions. The quantified or estimated thickness of the barrier membrane and/or the initial data associated with the gas exchange during the initial build up can also be used to evaluate other conditions as noted above.

In other embodiments, the response or behavior of the $^{129}$Xe during other portions of the analysis period can be used to evaluate ventilation/perfusion ratios. For example, the curve or line shown can be broken down into at least three characterizing parameter: the slope "m" corresponding to the linear rise in the signal after the initial portion of the signal, the time constant "$\tau$" associated with the initial portion of the signal, and the amplitude defined by a steady state amplitude of the signal deconvoluted from the data representing the signal at the t>> than the calculated time constant "$\tau$". In particular embodiments, the amplitude of the signal that is 37% greater than the amplitude of the signal at the time=$\tau$ can be used to represent oxygen saturation of ventilated blood. The slope "m" can be used as a measure of global xenon uptake (as a tracer for oxygen) in the blood. The slope of this curve ("m") may yield information about global blood flow to the ventilated portion of the lung and, hence, may be a predictor of shunt or cardiac output. Similarly, the amplitude of the $^{129}$Xe spectroscopic signal defined in relationship to the time constant can be used as a measure of oxygen saturation (ventilated blood volume). The time constant "$\tau$" can also be used to evaluate or determine the thickness, function, or physiology of the barrier or membrane.

In other embodiments, as shown in FIG. 5B the NMR signal of $^{129}$Xe in tissue can also be monitored to evaluate tissue volume (corresponding to the peak amplitude of the curve associated therewith) while the time constant "$\tau$" associated with the signal in tissue can be used as a measure of thickness. In certain embodiments the measured thickness can range from about 1 $\mu$m–100 $\mu$m.

The NMR signals and associated evaluations and measurements can be performed while the subject is substantially at rest and/or when the subject or patient is exposed to stress such as while exercising (or exposed to artificial stimulus elevating the heart beat rate and/or emulating other cardiopulmonary conditions).

In addition, in certain embodiments, the dynamic data provided by the polarized $^{129}$Xe an be used to monitor a therapy administered to the subject for efficacy or for drug development processes where a new drug or use is undergoing evaluation during clinical or pre-clinical trials.

FIGS. 5A and 5B illustrate simulated signal strength (peak area) in % over successively longer incrementally increasing inter-pulse delay times. The xenon transit time into the monitored frequency shift occurs at the initial portion of the curve.

Measurement of the xenon/blood resonance signal (S) or the xenon/tissue resonance (or other environment of interest) as a function of time ("S(t)") can be expressed by the following mathematical relationship:

$$S(t)=S_0(1-e^{-t/\tau}).$$  Equation (1)

Where "$\tau$" is the time constant for polarized $^{129}$Xe associated with the uptake and/or dissolved gas-exchange transit time, and "S" is the signal strength of the polarized $^{129}$Xe at the selected frequency (or in the bio-environment or bio-structure of interest). These time constants have been measured in dogs to be at about 61 ms and 70 ms for the tissue and blood compartments, respectively. See Ruppert et al., *NMR of Hyperpolarized $^{129}$Xe in the Canine Chest: Spectral Dynamics During a Breath-Hold*, 13 NMR in Biomedicine, p. 633–641 (2000). The time constants are representative of the amount of time it takes xenon to diffuse across the alveolar membrane and into the red blood cells. The diffusion constant of xenon in water is about $2\times10^{-5}$ cm$^2$/s. See Wolber et al., *Measuring Diffusion of Xenon in solution with hyperpolarized 129Xe NMR*, 296 Chemical Physics Letters, p. 391–396, (Nov. 6, 1998). The mean square distance traveled by a randomly diffusing gas can be approximated as described by Equation (2).

$$Z^2=2Dt.$$  Equation (2)

Where "$Z^2$" is the mean square distance, "D" is the diffusion coefficient constant and "t" is the time it takes the gas to diffuse through the membrane. Thus, from the two transit times measured above, mean thickness or diffusion distances of about 15.6 $\mu$m and about 16.7 $\mu$m can be calculated. It is noted that these curves are taken from the entire lung and include regions where tissue is thicker or thinner. Alternative pulse sequences can be used to identify the uptake in the first few milliseconds (the transmit times are typically under about 100 ms) corresponding to transit times across the thinnest membranes. At the onset of certain diseases, the mean transit time can become longer (or shorter). Because diffusion time is proportional to the square of the tissue thickness, the transit time will be sensitive for quantifying wall thickness and/or thickening (or thinning as the case may be).

Figure 6:
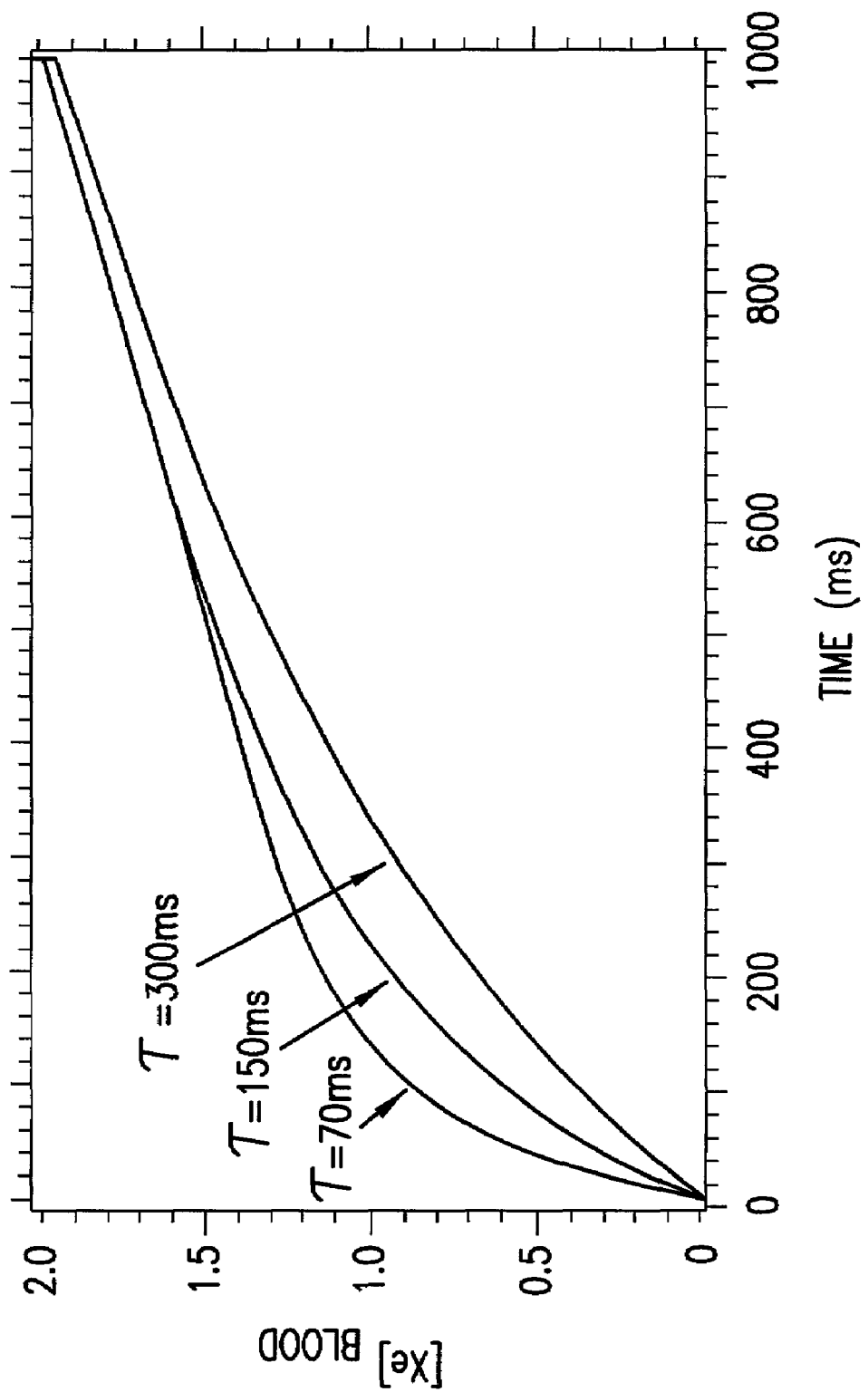
FIG. 6 is a graph of the uptake of polarized $^{129}$Xe in blood over time. The graph illustrates three different curves fit to the dynamic data, each representing a different dynamic gas behavior which can be evaluated to ascertain information about the patient according to embodiments of the present invention.

FIG. 6 illustrates graphs of curves having three different time constants for the polarized $^{129}$Xe signal in blood illustrating the cardiopulmonary functional change that may be representative of heart failure or other disorders, diseases, or conditions. The time constant can be calculated by Equation 1 and is typically defined at when the signal is at about 63% of its ultimate value. As shown, the time constant for each of the curves varies in a quantifiable manner. The longer time constants (i.e., $\tau$=150 and 300 ms) correspond to thicker alveolar-capillary membranes. In certain diseases or conditions, the alveolar membrane can thicken in response to hypertension or other conditions. As the condition deteriorates, the transit time or time constant "$\tau$" increases (shown as going from 70 ms to 300 ms) corresponding to the thickening of the alveolar membranes in response to hypertension and the like (reducing oxygen diffusing capability). Many therapeutic regimens attempt to change physiology of certain regions, organs, or structures of the body (such as to thin the alveolar membranes) and the present invention can assess whether this objective has been achieved by evaluating the time constant $\tau$ and/or other $^{129}$Xe signal parameter. Monitoring such a progression or behavior to confirm that the therapy is effective of that the condition is not deteriorating may provide important clinical information.

The signal strength of the dissolved phase polarized xenon signal intensity versus repetition time can have an associated slope "m" which is a function of the signal and the pulse repetition ($dS_p/dT_R$). In operation, a large flip angle pulse (preferably a flip angle of about 90 degrees) can be transmitted to the blood; this destroys all the magnetization in the xenon and, thus, the signal of the dissolved polarized xenon in the blood. Subsequently, after the excitation pulse, additional polarized $^{129}$Xe is taken-up in the blood (replenished) over time until a substantially steady state level is reached: the more polarized xenon in the blood, the larger or stronger the associated signal. This increase in the dissolved phase xenon signal over time (after the initial transit time across the barrier) can be mathematically represented by the slope of the line ($dS_p/dT_R$). The slope (after an initial gas blood barrier crossing period) can be directly proportional to blood flow rate (Q) in the bloodstream.

In order to determine the slope of the line associated with the signal of the dissolved phase xenon in the blood over time, the data acquisition can obtain several data points such as three-ten temporally separate data points within the first 60 ms to establish the time constant associated with the curve fit of the signal shape/$^{129}$Xe behavior at the peak(s) of interest. In certain embodiments, it will take longer for blood to uptake polarized xenon where there is low blood flow in ventilated regions in the lung and a shallower blood signal slope may be indicated (representing a low blood flow rate in ventilated regions of the lung or other region).

In certain embodiments, the slope data of the dissolved phase polarized $^{129}$Xe in tissue and/or blood versus can be adjusted by comparing it to the gas phase signal in the lung ($S_L$). This gas phase signal ($S_L$) is acquired from an excitation signal with a known flip angle $\forall_L$ (the polarized gas is conveniently available in the lung space). Thus, the present invention can use a mathematical relationship between the dissolved phase polarized xenon signal in the blood or tissue with the xenon signal in the gaseous phase in the lung to establish a quantitative measure of signal.

In particular embodiments, a lung volume ($V_L$) is measured by conventional means before or after the MR procedures, or by assuming an average or normalized lung volume for a particular patient size or age. After a short initial time, the slope of the curve corresponds to the blood flow rate in the blood stream.

In summary, according to certain embodiments of the present invention, there are several quantifiable parameters that can be derived from the $^{129}$Xe uptake spectra: $S_{peak}$ (tissue), $\tau$(tissue), $S_{peak}$(blood), $\tau$(blood), and slope of the linear uptake portion of the xenon/blood resonance. These uptake spectra may be performed on a regional basis in the lung. This dynamic signal data can be obtained with millisecond or better resolution. In certain embodiments, the alveolar transit time, oxygen saturation level, global perfusion, tissue volume and ejection fraction can be evaluated to identify any abnormalities or alterations in physiology or function.

Generally stated, the ventilated blood flows to the heart to the left atrium to the left ventricle and pumped to body through the (arch of) aorta. The blood is forced or ejected from the heart in pulsatile flow corresponding to the pumping action thereof. The pulsatile flow behavior of the blood ejected from the aorta can be monitored to evaluate or map the ejection fraction. Gradient-tagged RF excitation pulses can be used to look at the signal of the $^{129}$Xe in the blood as it exits the aorta or left ventricle (or region proximate thereto). This targeted region can be monitored to obtain the signal strength of the $^{129}$Xe in this ejected blood over time, the signal will increase and decrease corresponding to the cardiac cycle and the signal can be evaluated to assess how much of the polarized blood is pumped out of the left ventricle or aorta in each pumping cycle. This ejection fraction can be compared to the subject's own previous evaluation or based on a statistical population average (by gender and/or age which can be generally stated to be an average of about 60%) to asses whether there is an abnormality. Thus, for example, if 200 ml of ventilated (polarized) blood is pumped into the heart and 100 ml is ejected, the ejection fraction may be identified as 50% (lower than average). Thus, in certain embodiments, the dynamic gas exchange data of signal over time in one, two, or more different environments, regions, or tissues (such as tissue and blood) can provide information on ventilation, perfusion, and ejection fraction, as noted above.

Figure 7B:
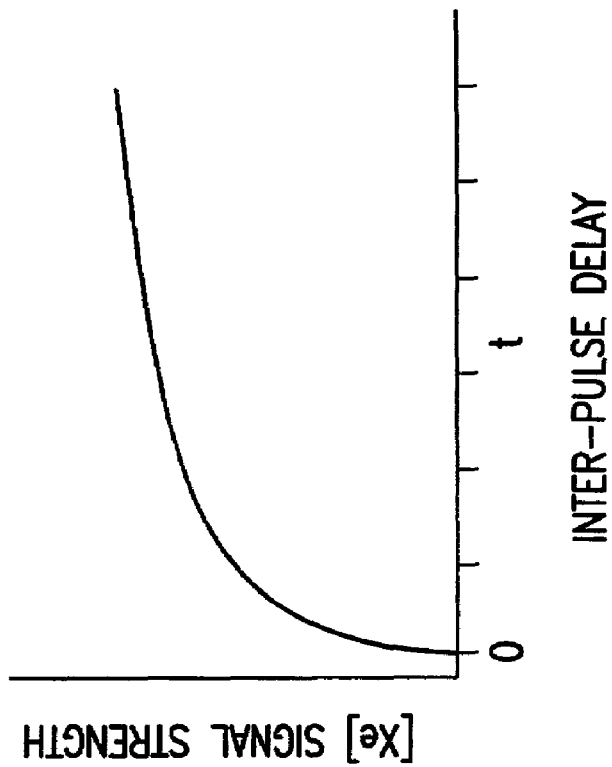
FIG. 7A is a polarized gas $^{129}$Xe measure of ventilation distribution MRI image of the lungs and FIG. 7B is a graph of the polarized $^{129}$Xe uptake over time; each can be generated based on a single-breath or ventilation administration of the polarized $^{129}$Xe according to embodiments of the present invention.
Figure 7A:

In addition, as shown in FIGS. 7A and 7B, in certain embodiments, there may be enough magnetization or polarization associated with the $^{129}$Xe in vivo to perform a polarized $^{129}$Xe ventilation or $^1$H MRI ventilation image in the same breath-hold period, typically of about 10 seconds. The combination image/scan with the spectroscopic analysis can provide additional information on the state of the cardiopulmonary system. In certain embodiments, the test can be carried out in an MRI magnet with a dual-tuned $^{129}$Xe/$^1$H coil to allow conventional or standard imaging to be performed to yield anatomical information in the same MR imaging/spectroscopy session. It is noted that the image shown is based on polarized $^3$He because it is readily accessible, but it is anticipated that a similar resolution ventilation image can be generated using polarized $^{129}$Xe.

The barrier 10 can be a wall, membrane, lining, tissue, red blood cell, or other structure, fluid, or environment in the body. In certain embodiments the gas-exchange dynamics of membranes can be evaluated using the dynamic data sets of polarized $^{129}$Xe.

Particular embodiments of the present invention are directed to methods of evaluating the dynamic behavior of the polarized $^{129}$Xe in a target region in the body to evaluate the cerebral perfusion of a subject, or other structures or membranes for dysfunctions. The polarized $^{129}$Xe can be used to determine one or more of whether low oxygen saturation is the result of poor ventilation, poor perfusion, and/or poor gas diffusing capacity across the alveolar membrane. Such an analysis can be used to diagnose chronic heart failure, to differentiate uncertain aetiology of breathlessness such as to identify cardiac or respiratory origin, to determine the adequacy of the alveolar-capillary unit, and to monitor therapeutic efficacy of treatments on those conditions.

For example, upon presentation to respiratory physicians, many patients exhibit a shortness of breath of uncertain aetiology. Thus, in certain embodiments, the present invention allows for evaluations of the adequacy of the alveolar-capillary unit using polarized $^{129}$Xe in a manner that can be useful to allow proper diagnosis and treatment. Potential clinical indications which can be assessed by methods of the present invention include, but are not limited to, the presence and/or extent of emphysema, the presence and/or extent of alveolitis (and follow-up monitoring for same), to differentiate pure airway conditions from conditions which affect the alveolar airspaces, the diagnosis of alveolar hemorrhagic conditions, and the diagnosis of radiation pneumonitis.

Figure 8A:
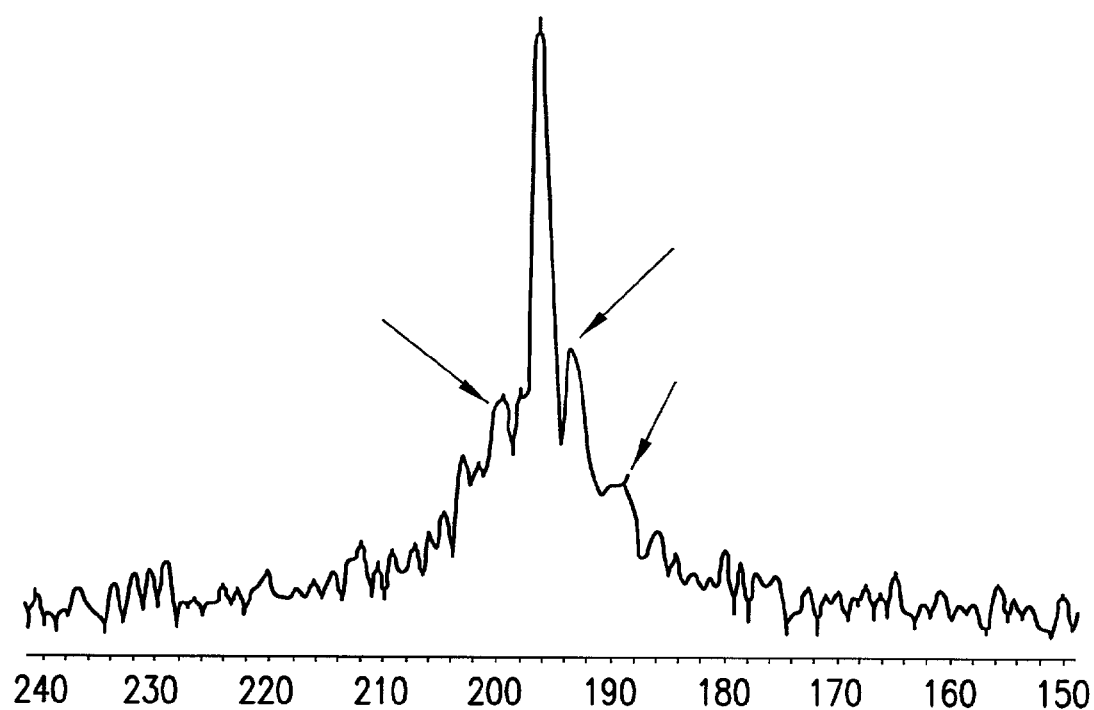
FIGS. 8A and 8C illustrate the perfusion signal amplitude data at a plurality of frequencies for the chemical shifts of brain tissue and/or cerebral blood flow shown in FIG. 8B.
Figure 8C:
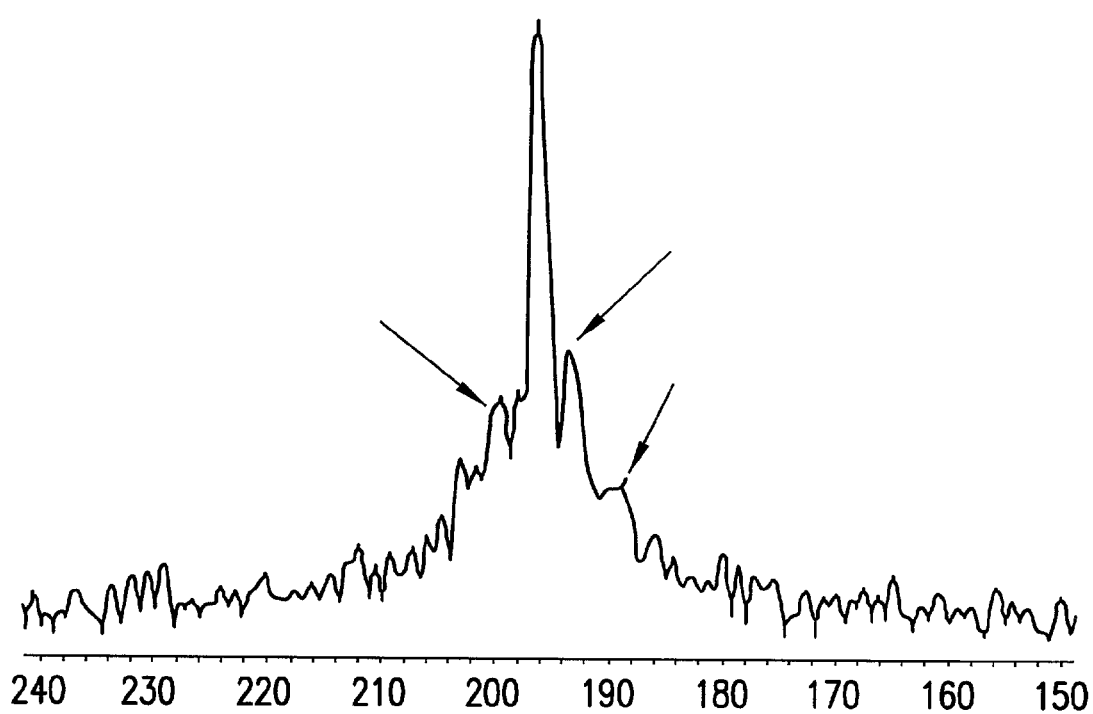
Figure 8B:
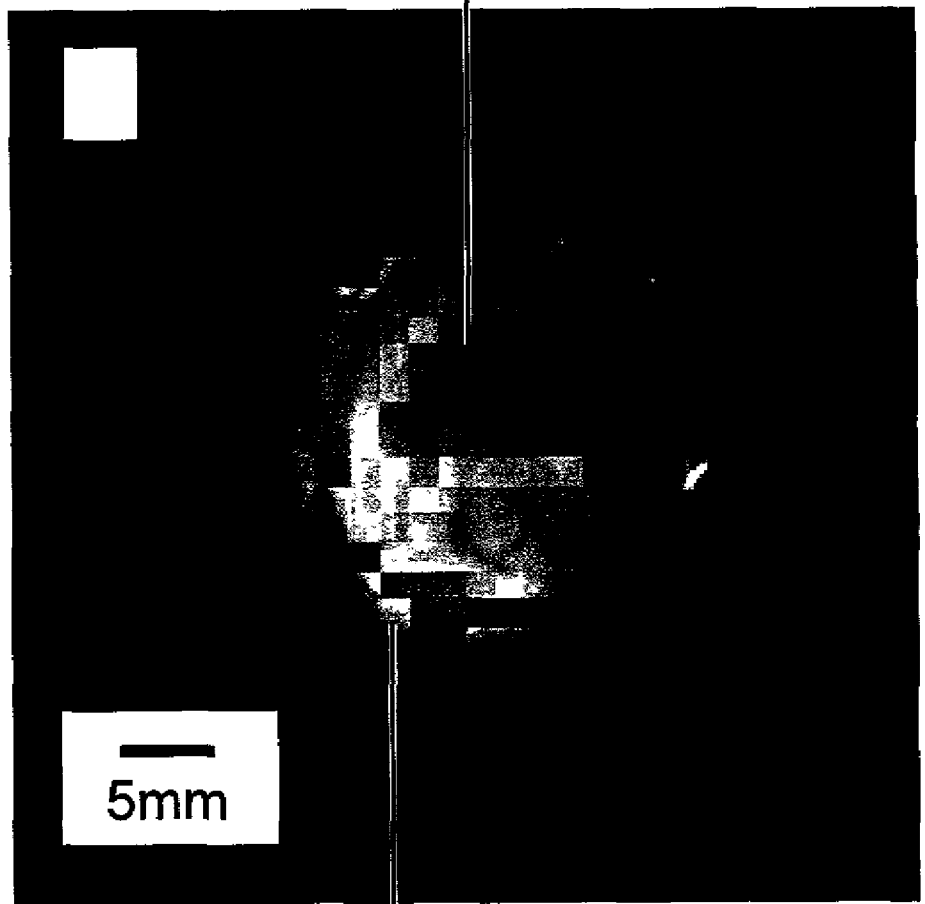
FIG. 8B is an image of the brain wherein each voxel (3-D pixel) represents/measures the perfusion associated with a plurality of NMR frequencies simultaneously according to embodiments of the present invention.

FIGS. 8A–8C illustrate another exemplary embodiment, where regional cerebral perfusion can be evaluated. FIGS. 8A and 8C are spectra of the polarized xenon at different locations (compartments) in the brain. The various peaks in the spectroscopic spectrums illustrate that a plurality of dynamic data sets (one for each of two, or more peaks shown by the three arrows pointed at certain peak positions) may be concurrently obtained at each compartment. This can be repeated to provide a cerebral perfusion map. That is, a simultaneous presentation of multiple peaks associated with perfusion in the brain. The peaks may correspond to gray matter, white matter, and the like. The perfusion data provided by the dynamic data can be used to construct a perfusion image of the brain where each voxel measures or quantifies a perfusion of a number of compartments simultaneously with moderate resolution (shown as about 5 mm or 1 cm$^3$). Such information can evaluate regional cerebral blood flow, white matter perfusion, gray matter perfusion, demylenation, and hypoxia or stroke. The cerebral perfusion image can combine the signal strength information of the multiple data sets or can be used separately to provide three different perfusion maps of the brain based on data obtained concurrently.

Figure 9:
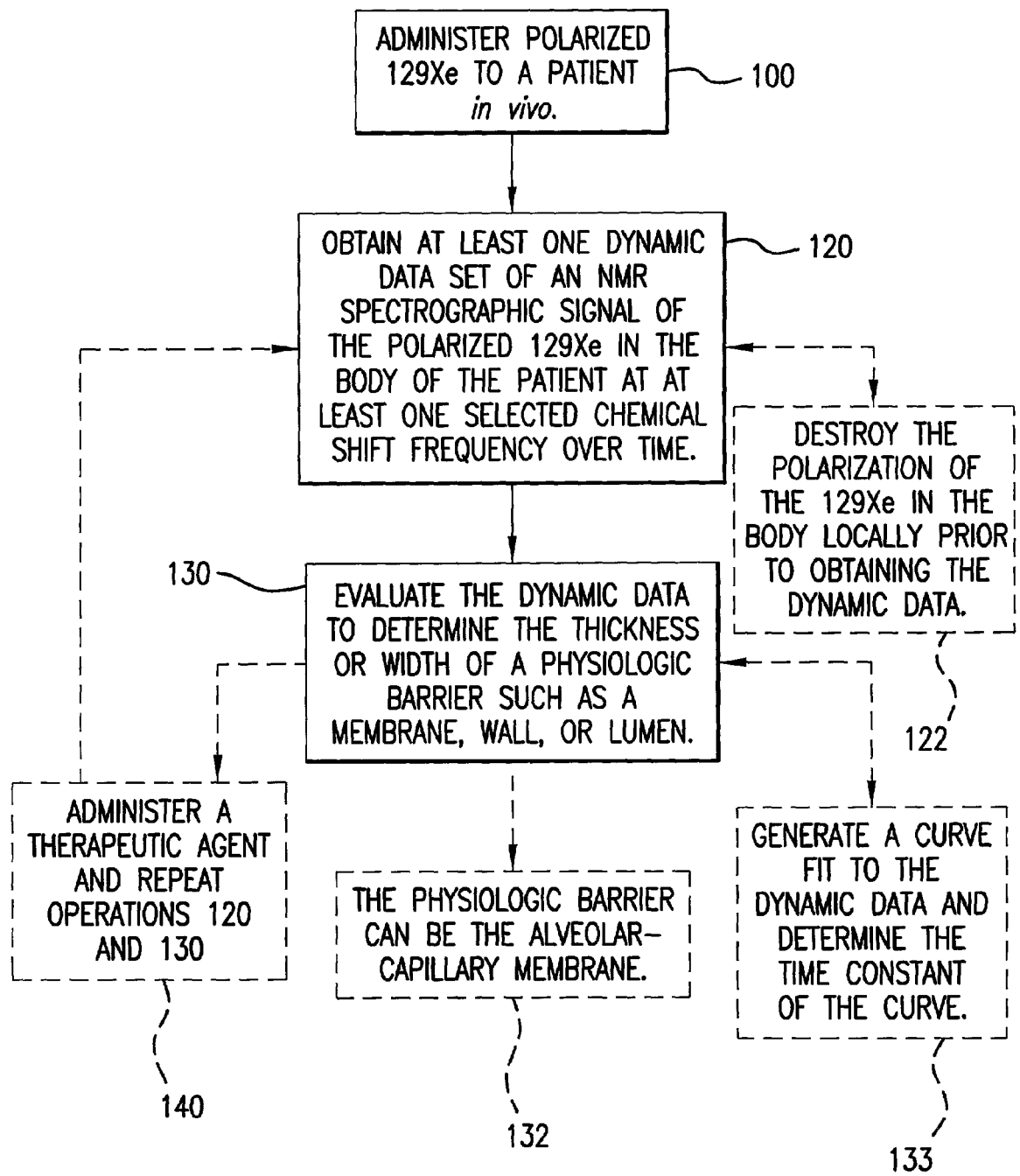
FIG. 9 is a flow chart illustrating one embodiment of operations for a method for spectroscopic analysis according to the present invention.

FIG. 9 is a flow chart of operations according to certain embodiments of the present invention. As shown, polarized $^{129}$Xe is administered to a patient in vivo (block 100). At least one dynamic data set of signal strength over time of an NMR spectrographic signal of the polarized $^{129}$Xe in the body of the patient is obtained at at least one selected chemical shift frequency (resonance) (block 120). A plurality of concurrent dynamic data sets can be obtained for different resonances, as desired. The polarization of the $^{129}$Xe can be destroyed locally prior to the obtaining the dynamic data (block 122). The dynamic data can be evaluated to determine the thickness or width of a physiologic barrier such as a membrane, wall, or lumen (block 130). A curve of signal strength over time can be generated to statistically "best-fit" the dynamic data (block 133) and a time constant associated therewith can be determined (block 133). A therapeutic agent can be administered and the operations described in blocks 120 and 130 can be repeated. The data for each can be compared to evaluate any alterations in the thickness or width (block 140). The physiologic barrier can be the alveolar-capillary membrane (block 132) or other membranes, or linings, walls, lumens, or structures or fluid environments in the body.

Figure 10:
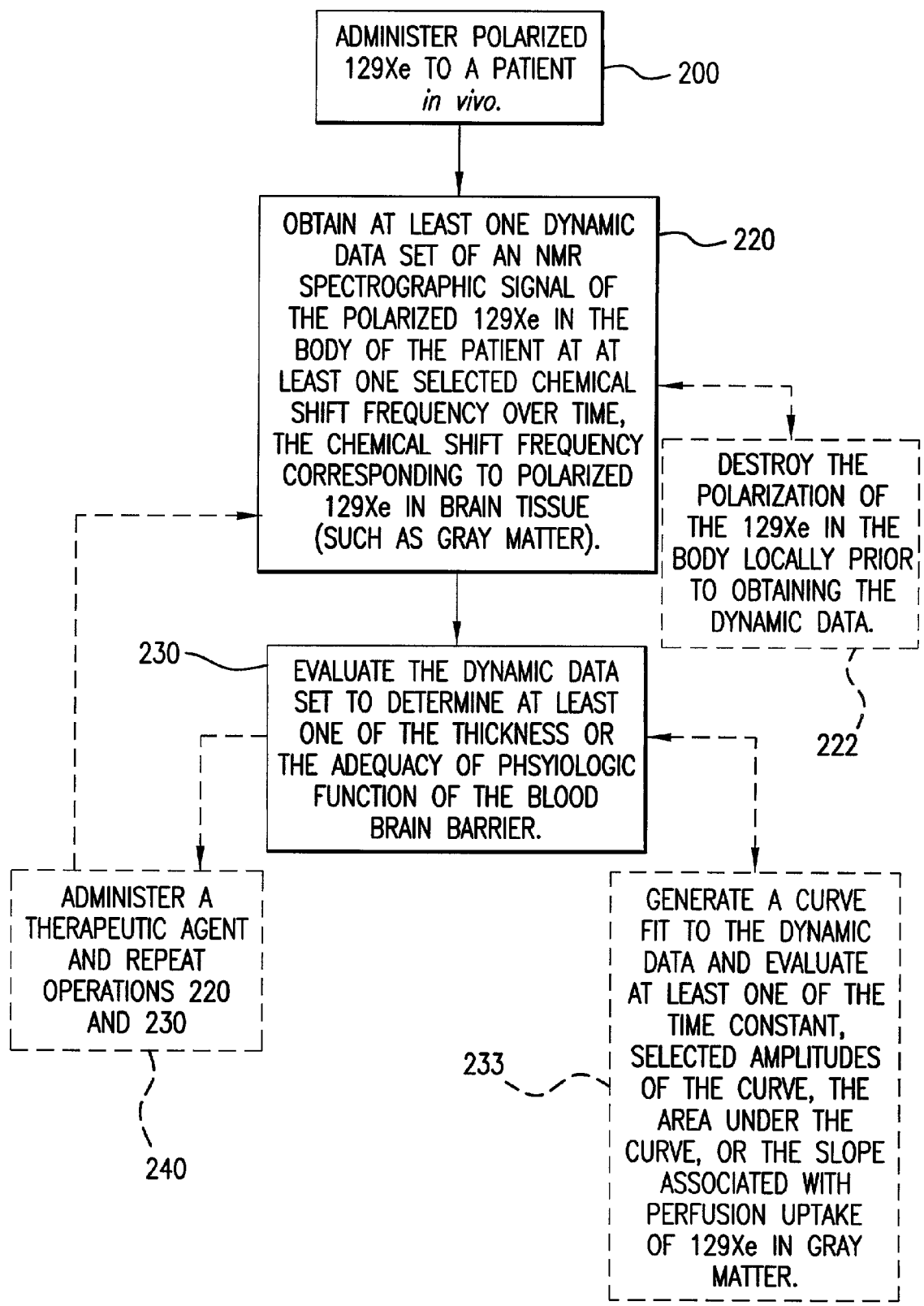
FIG. 10 is a flow chart illustrating one embodiment of operations for a method for spectroscopic analysis according to the present invention.

FIG. 10 illustrates the operations of another embodiment of the present invention. As before, polarized $^{129}$Xe is administered to a patient in vivo (block 200). At least one dynamic data set of an NMR spectrographic signal of the polarized $^{129}$Xe in the body of the patient at at least one selected chemical shift frequency over time is obtained. The chemical shift frequency or resonance can be selected to correspond to brain tissue (such as gray matter or white matter). As before, the polarization of the $^{129}$Xe can be destroyed locally proximate the brain tissue prior to initiating the obtaining step (block 222). The dynamic data can be evaluated to determine at least one of the thickness or adequacy of the function of the blood brain barrier function (block 230). A curve can be generated to fit the dynamic data and certain characterizing parameters can be evaluated. For example, the time constant, selected amplitude(s) of the curve, the area under the curve, the slope associated with the perfusion uptake into the brain (white or gray matter or cerebral blood) (block 233). A therapeutic agent can be administered to the patient and the operations recited in blocks 220 and 230 can be repeated (block 240). The dynamic data from the first and repeated steps can be compared to evaluate efficacy or impact on the patient.

In certain embodiments, polarized $^{129}$Xe is delivered to the brain via the blood stream and crosses the blood brain barrier to diffuse into brain tissue. Thus, the polarization can be destroyed and then the NMR signal strength over time associated with uptake of $^{129}$Xe in one or more brain tissue components can be monitored to assess blood brain barrier function and/or thickness or physiology.

Figure 11:
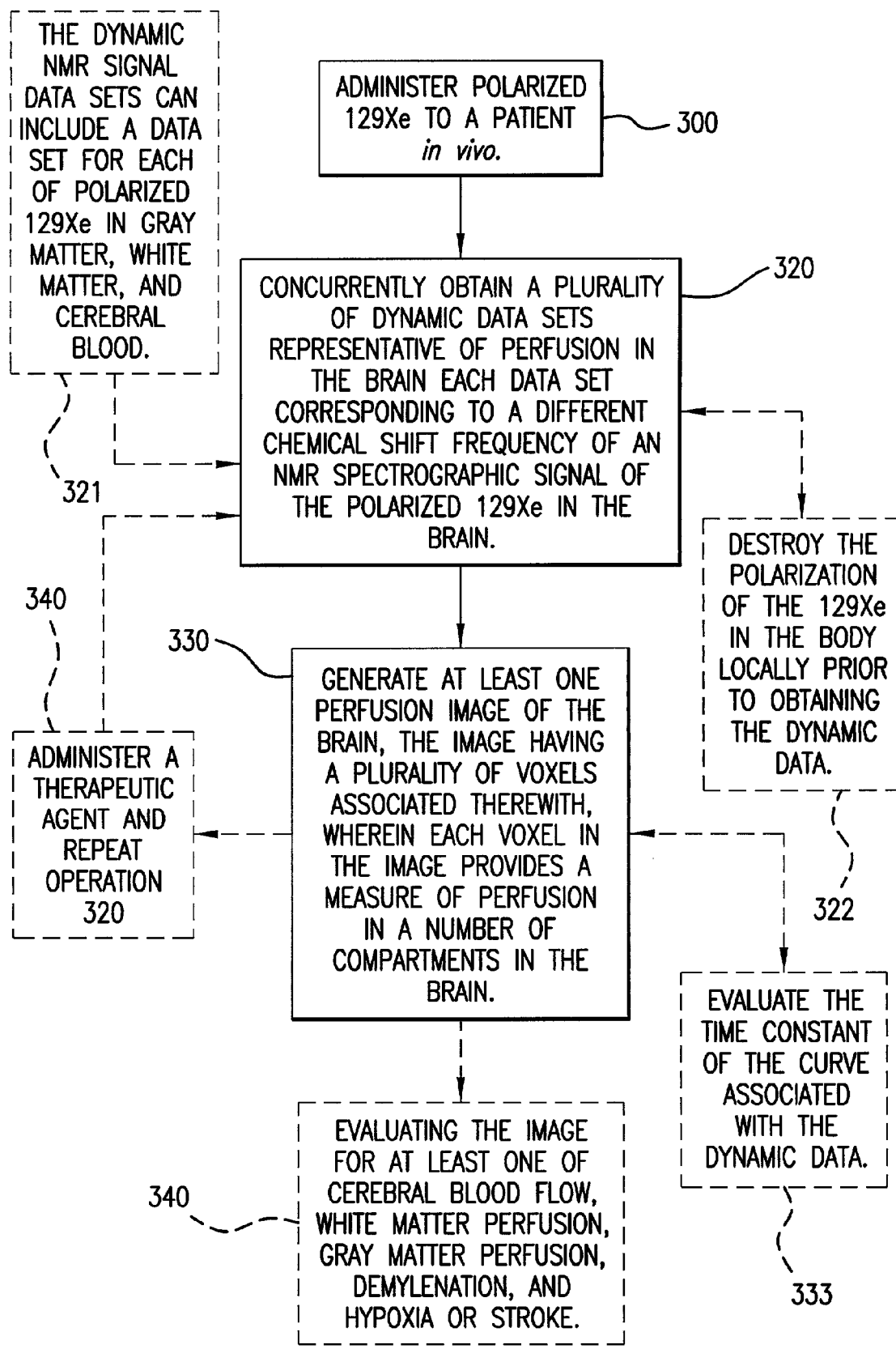
FIG. 11 is a flow chart illustrating one embodiment of operations for a method for spectroscopic analysis according to the present invention.

FIG. 11 is a flow diagram of operations of yet another embodiment. As before, polarized $^{129}$Xe is administered to the subject or patient (block 300). Then a plurality of dynamic data sets are obtained concurrently, each of the dynamic data sets being representative of a different chemical shift frequency of an NMR spectrographic signal of the polarized $^{129}$Xe in the brain. As before the polarization of the $^{129}$Xe can be destroyed prior to commencing the obtaining operation (block 322). At least one cerebral perfusion image can be generated mapping the perfusion in the brain associated with a plurality of different brain constituents (block 330). The data sets can represent polarized $^{129}$Xe in gray matter, white matter, and cerebral blood (block 321). The image includes a plurality of voxels, the spectrum associated with each voxel provides a measure of perfusion for a number of ('n') compartments simultaneously. As before a curve can be fit to the dynamic data and a time constant determined (block 333). The image and/or dynamic data can be evaluated for at least one of ventilated cerebral blood flow, white matter perfusion, gray matter perfusion, demylenation, and hypoxia, or stroke (block 340). A therapeutic agent can be administered to the patient and the step of obtaining the dynamic data sets repeated (block 340) to evaluate the progression of disease, the efficacy of treatment and the like. Of course, the step can be repeated without administering a pharmaceutical or therapeutic agent to monitor disease, or progressive conditions.

Figure 12:
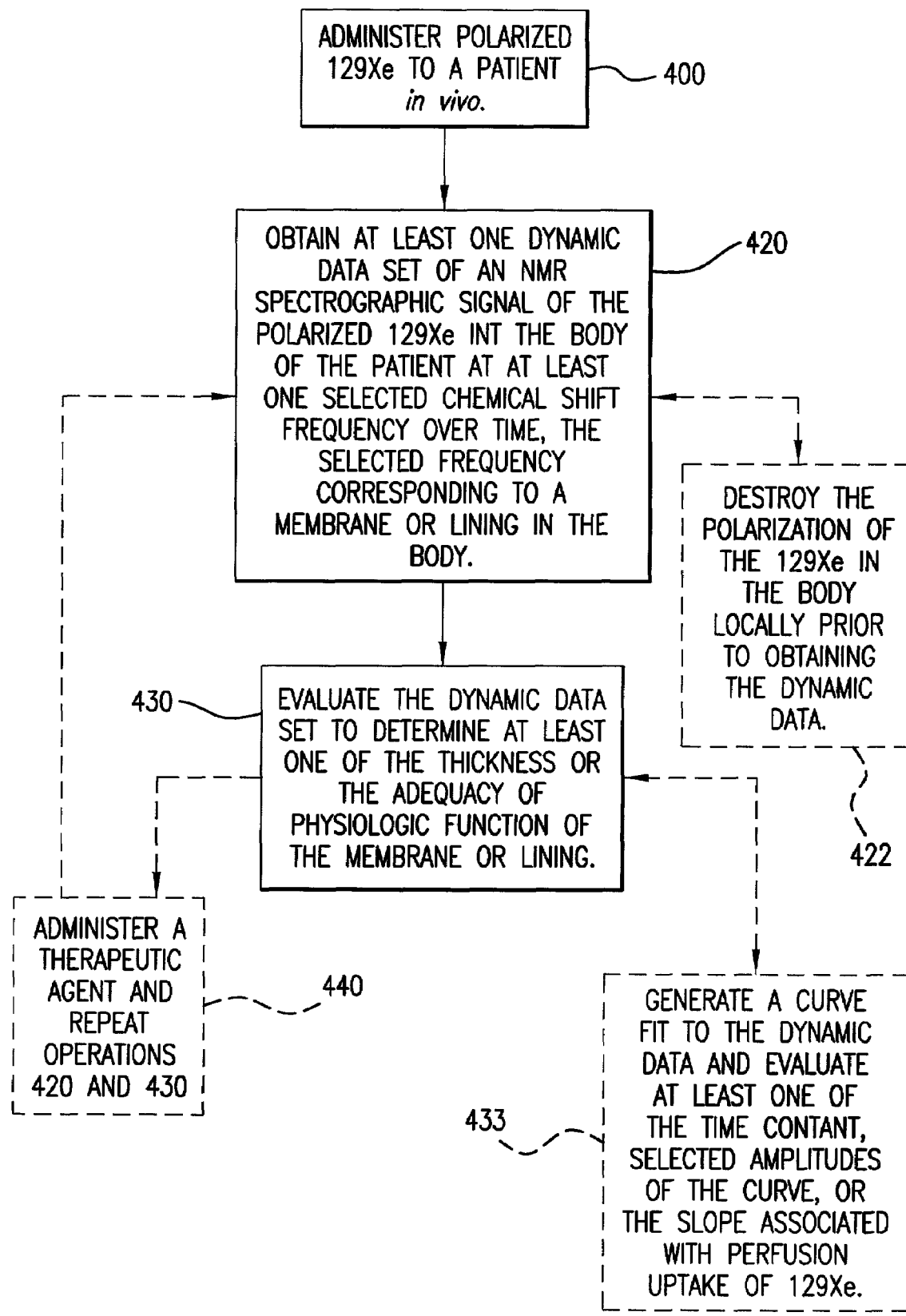
FIG. 12 is a flow chart illustrating one embodiment of operations for a method for spectroscopic analysis according to the present invention.

FIG. 12 illustrates yet another embodiment of operations. Again, polarized $^{129}$Xe is administered to the subject (block 400). At least one dynamic data set of signa strength over time of an NMR spectroscopic signal of the polarized $^{129}$Xe in the body of the patient is obtained at at least one selected chemical shift frequency or resonance, the selected frequency corresponding to a membrane or lining in the body (block 420). Also, as before, the polarization of the $^{129}$Xe can be destroyed locally prior to initiating the obtaining step (block 422). The dynamic data set can be evaluated to determine at least one of the thickness or adequacy of the membrane or lining (block 430). Again a curve can be fitted to the dynamic data and at least one of several characterizing parameters evaluated: including, for example, the time constant, selected amplitudes of the curve (such as peak or at t>>τ), or the slope associated with perfusion uptake of $^{129}$Xe (block 433). A therapeutic agent can be administered and the operations described in blocks 420 and 430 repeated (block 440).

Generally stated, in operation, a patient is positioned in an MRI unit and exposed to a magnetic field. The MRI unit typically includes a super-conducting magnet, gradient coils (with associated power supplies), an NMR coil (transmit/receive RF coil), and a RF amplifier for generating RF pulses set at predetermined frequencies. For $^{129}$Xe imaging at 1.5T field strength, the MRI unit is set to operate in the gas-phase at about 17.6 MHz. The dissolved phase excitation frequency is shifted below the gas phase excitation frequency such as between about 196 to at least 200 ppm lower than the gas phase excitation frequency (corresponding to the chemical shift). Thus, the dissolved phase $^{129}$Xe RF excitation frequency can be about 3.52 kHz lower than the associated gas-phase excitation frequency. In other embodiments, the imaging method employs a 17.6 MHz gas phase excitation pulse and an associated dissolved phase excitation pulse of about 17.59648 MHz. Of course, the magnet field strength and excitation frequency can vary, as is well known to those of skill in the art depending on the target region/tissue or environment undergoing evaluation.

In any event, the RF pulse(s) is transmitted to the patient to excite the nuclei of the polarized $^{129}$Xe. The NMR coil is tuned to a selected frequency range and positioned adjacent the targeted imaging region to transmit the excitation pulses and to detect responses to the pulse sequence generated by the MRI unit. NMR coils for standard chest imaging can include a wrap-around coil with conductors positioned on both the front and back of the chest. Examples of acceptable coils known to those of skill in the art include a bird-cage configuration, a Helmholtz pair, a surface coil, and a solenoid coil (for permanent magnets). Other surface coils can be used for other imaging regions of the body (such as the head, torso, and the like).

In certain embodiments, the patient can inhale a quantity of polarized $^{129}$Xe gas into the pulmonary region (i.e., lungs and trachea). After inhalation, the patient can hold his or her breath for a predetermined time, such as 5–20 seconds. This can be described as a "breath-hold" delivery. Examples of suitable "single dose" quantities of polarized gases for breath-hold delivery include 0.25–0.5, 0.75, and 1.0–2.0 liters of gas. The dose at inhalation can contain gas with a suitable polarization level, typically so that the polarization at delivery is well above 5%, and preferably a polarization level above about 20%–50%.

In overview, according to embodiments of the instant invention, shortly after inhalation of a suitable amount of hyperpolarized $^{129}$Xe gas (or gas mixture), the MRI unit can deliver a suitable excitation pulse. In particular embodiments, the excitation pulse can be a large flip angle RF excitation pulse to a selected portion of the pulmonary vasculature. As used herein, "large flip angle" means an angle that is greater than about 30 degrees, and typically greater than about 75 degrees, and more typically about 90 degrees. A 30-degree flip angle will generally yield about 50% as much signal as a 90-degree flip (45 degrees typically giving about 70% as much signal).

The RF excitation can be selectively performed. "Selective excitation" is generated such that it excites only certain frequencies, i.e., that it excites substantially only the dissolved phase polarized gas. An exemplary delivery of a selective excitation pulse is via a "hard" pulse. As used herein, "hard" pulse includes pulses where the RF is turned on for a short pulse time ("$t_{pulse}$") and then shortly thereafter, indeed preferably substantially "instantly," turned off. However, short pulse times can yield uncertainty in the associated frequency it generates. In certain embodiments, selective excitation is performed such that the pulse frequency is centered on the dissolved gas phase resonance desired (i.e., 17.59648 MHz) and has a pulse time, $t_{pulse}$, such that the associated frequency is below the corresponding gas phase excitation frequency (i.e., 17.6 MHz). For example, one frequency spectrum of a square excitation pulse having a time $t_{pulse}$ and which is centered on a frequency ("fo") can be described by the equation:

$$\sin(a(f-fo)/a(f-fo)), \text{ where } a=3.1416*t_{pulse}. \quad \text{(Equation 3)}$$

Therefore, the pulse time $t_{pulse}$ is preferably set so that the sin (a(f–fo))=0 for the gas phase component. Stated differently, the pulse time $t_{pulse}$ is determined according to the relationship $t_{pulse}=1/(f-fo)$. In one embodiment, for a 1.5 T magnetic field strength, f–fo equals 3.52 kHz and $t_{pulse}$ is about 284 μseconds ($10^{-6}$). Of course, as will be recognized by those of skill in the art, alternative approaches can also be used, such as, but not limited to, sine pulses, gaussian pulses, and the like.

In certain embodiments, a large flip angle pulse is delivered to the target region so as to substantially destroy the incoming $^{129}$Xe polarization or magnetization to set the "0" or monitoring start window for analyzing the transit time and/or polarized $^{129}$Xe behavior/exchange dynamics. Thereafter, in certain embodiments, the selective excitation is timed such that it excites the entire pulmonary blood volume. The pulmonary blood volume includes the volume of blood that fills the blood passages associated with the circulatory system between and/or within the lungs and the heart (which can include the volume of blood or a portion of the volume of blood within the boundary lung tissue and/or heart). Advantageously, unlike imaging the gas-phase $^{129}$Xe in the lung where conventionally small flip angles are used to avoid destroying the available magnetization, a large flip angle excitation of the dissolved phase $^{129}$Xe in the pulmonary vasculature allows for the initialization of the "0" level to monitor the gas-exchange dynamics. Further, according to the certain embodiments using inhalation delivery of the $^{129}$Xe, "fresh" magnetization (i.e., polarized $^{129}$Xe) is substantially continuously flowing in from the capillary beds during the procedure. See co-assigned and co-pending U.S. patent application Ser. No. 09/271,476 and U.S. patent application Ser. No. 09/271,476 for descriptions of imaging methods using $^{129}$Xe. The contents of these documents are hereby incorporated by reference as if recited in full herein.

The term "pulmonary and cardiac vasculature" as used herein includes all of the blood vessels within the lungs and/or heart, the chambers of the heart, the passages between the chambers of the heart, as well as the blood vessels between the lungs and heart, and blood vessels between the lungs or heart and other tissues and/or organs. The pulmonary and cardiac vasculature includes, but is not limited to, the pulmonary veins and arteries and associated capillaries, the left and right atria of the heart, the left and right ventricles of the heart, the myocardium, the aorta and aortic arch, the coronary artery, the coronary arteries, the subclavian arteries, and the carotid arteries.

Almost immediately upon inhalation of hyperpolarized $^{129}$Xe into the lungs, Xe begins to dissolve into the pulmonary blood stream (typically in under about 100 ms). The concentration of Xe in the pulmonary capillary beds ("$[Xe]_P$") can be assumed to equilibrate after an initial gas transit time (as the gas travels across the alveolar-capillary membrane) with the concentration of Xe in the lung gas spaces ("$[Xe]_L$"). Thus, the relationship can be stated as:

$$[Xe]_P = 8[Xe]_L, \quad \text{(Equation 4)}$$

where "8" is the Xe blood/gas partition coefficient or blood solubility. This concentration can be expected to equilibrate in the venous side of the pulmonary vasculature just a few seconds after inhalation. The standard unit for concentration is an "amagat" which refers to 1 atmosphere of gas pressure at a temperature of 273 K. For humans whose lungs contain one atmosphere of gas and whose temperature is about 310 K, all gas densities should be scaled down by a factor of about A=0.88 amagat per atmosphere. For a patient inhaling a volume ("$V_{Xe}$") of Xe into their lungs of volume ("$V_L$"), the resulting Xe density in the lung $[Xe]_L$ will be $$[Xe]_L = A \frac{V_{Xe}}{V_L}. \quad \text{(Equation 5)}$$

Thus, the concentration of Xe in the pulmonary blood $[Xe]_p$ will be related to the inhaled gas volume $V_{Xe}$, and can be stated by the expression:

$$[Xe]_P = \lambda A \frac{V_{Xe}}{V_L}. \quad \text{(Equation 6)}$$

For reference, an estimate of λ for Xe in blood is that 8≈0.15. Thus, as an example, a patient who inhales 1 L of Xe into his 6 L lung will yield a Xe density in the lungs of $[Xe]_L \approx 0.15$ amagat, and correspondingly a Xe density in the pulmonary capillary beds of $[Xe]_P \approx 0.02$ amagat. Thus, the dissolved polarized $^{129}$Xe gas in the pulmonary capillary beds will saturate at approximately 1/6 the concentration of the lung gas.

In certain embodiments, the present invention provides perfusion images that can be two (2) and three (3) dimensional multi-peak dissolved phase images of the perfusion in selected regions of the body such as the pulmonary vasculature or selected tissue in the brain (FIG. 8B) and the like.

As described in co-pending U.S. patent application Ser. No. 09/271,476, incorporated by reference as if recited in full herein, a patient who inhales 1 L of Xe into the lungs (having about a 6 L lung volume) will yield about or dissolve into about 1/6 of that value of the xenon concentration (0.02 amagat) in the pulmonary vasculature and associated blood. In certain embodiments, the method uses frequency selective large angle (more preferably 90°) RF excitation pulses that substantially deplete the $^{129}$Xe in the pulmonary blood but leave the hyperpolarized gas in the lungs substantially undisturbed to define the initial monitoring period during which dynamic NMR signal data is obtained. In this embodiment, the repetition time interval between RF pulses ($T_R$) and the pulmonary blood flow rate (Q) can be used to determine the effective pulmonary volume ($V_{eff}$) containing (dissolved phase) hyperpolarized $^{129}$Xe. This relationship assumes that $T_R$ is less than or substantially equal to the time it takes for the polarized $^{129}$Xe to leave the pulmonary blood ($t_p$). As discussed above, for typical blood flow rate and estimated volume of venous pulmonary blood, $t_p$ is approximately 2.5 seconds. Thus, with a large RF excitation pulse (preferably, about α=90°), the dissolved pulmonary $^{129}$Xe signal strength in the pulmonary blood is proportional to the product of coil gain ("G"), Xe polarization ("$P_{xe}$"), and polarized Xe density or concentration in the vasculature ($[Xe]_P=\lambda[Xe]_L$), which can be stated by the following expression:

$$Sp(T_R)=GP_{Xe}8[Xe]_L QT_R. \quad \text{Equation (7)}$$

Notably, the signal strength is dependent on both the pulse interval ($T_R$) and the blood flow rate (Q). The dissolved signal intensity versus repetition time will have an associated slope which can be mathematically expressed as follows:

$$\frac{dS_P}{dT_R} = GP_{Xe}\lambda[Xe]_L Q.$$ Equation (8)

The slope "m" of polarized xenon in the pulmonary blood is directly proportional to the pulmonary blood flow rate (Q). Calibration of the blood flow rate is obtainable by evaluating the gas phase signal ("$S_L$") in the lung, the signal having an associated small RF tipping angle (excitation angle) ("$\alpha_L$"). The gas phase signal can be expressed by the equation:

$$S_L = GP_{Xe}[Xe]_L V_L \sin \alpha_L.$$ Equation (9)

The pulmonary blood flow rate (Q) can be stated by the ratio of the hyperpolarized $^{129}$Xe gas and dissolved phase signals. This ratio cancels receiver gain (G) and polarization value $P_{xe}$. Accordingly, the blood flow rate (Q) can be expressed by the following:

$$Q = \frac{V_L \sin\alpha_L \left(\frac{dS_P}{dT_R}\right)}{\lambda S_L}.$$ Equation (10)

Advantageously, with measurements of the Xe/blood partition coefficient ($\lambda$) and the total lung volume ($V_L$), a quantitative measurement of blood flow is established according to a method of the instant invention. As will be appreciated by one of skill in the art, lung volume can be easily established to about 20% accuracy with techniques known to those of skill in the art. Preferably, techniques with relatively improved accuracy such as but not limited to spirometry are used.

The spectroscopic evaluation methods do not require a polarization calibration because the measurement can be "self-calibrating." Stated differently, the polarization can be cancelled by comparing dissolved and gaseous xenon signal, both of which can be assumed to have substantially the same or identical polarization to the extent that T1 relaxation in the blood is negligible, which it is for short $T_R$ settings as discussed above.

The present invention has been described above with respect to particular preferred embodiments. Those skilled in the art, however, will appreciate that the invention can be employed for a broad range of applications. Methods for imaging or obtaining information about gas exchange barriers or environments and/or perfusion mapping using dissolved hyperpolarized $^{129}$Xe can be carried out according to the present invention using magnetic resonance or spectroscopic techniques known to those skilled in the art. See, e.g., U.S. Pat. No. 5,833,947; U.S. Pat. No. 5,522,390; U.S. Pat. No. 5,509,412'  U.S. Pat. No. 5,494,655, U.S. Pat. No. 5,352,979; and U.S. Pat. No. 5,190,744. See also Hou et al., *Optimization of Fast Acquisition Methods for Whole-Brain Relative Cerebral Blood Volume (rCBV) Mapping with Susceptibility Contrast Agents*, 9 J. Magnetic Resonance Imaging 233 (1999); Simonsen et al., *CBF and CBV Measurements by USPIO Bolus Tracking: Reproducibility and Comparison with Gd-Based Values*, 9 J. Magnetic Resonance Imaging 342 (1999); Mugler III et al., *MR Imaging and Spectroscopy Using Hyperpolarized $^{129}$Xe gas: Preliminary Human Results*, 37 Magnetic Resonance in Medicine, pp. 809–815 (1997); Belliveau et al., *Functional Cerebral Imaging by Susceptibility-Contrast NMR*, 14 Magnetic Resonance in Medicine 14 538 (1990); Detre et al., *Measurement of Regional Cerebral Blood Flow in Cat Brain Using Intracarotid $^2H_2O$ and $^2H$ NMR Imaging*, 14 Magnetic Resonance in Medicine 389 (1990); Frank et al., *Dynamic Dysprosium-DTPA-BMA Enhanced MRI of the Occipital Cortex; Functional Imaging in Visually Impaired Monkeys by PET and MRI* (Abstract), Ninth Annual Scientific Meeting and Exhibition of the Society of Magnetic Resonance In Medicine (Aug. 18–24, 1990); Le Bihan, *Magnetic Resonance Imaging of Perfusion*, 14 Magnetic Resonance in Medicine 283 (1990); and Rosen et al., *Perfusion Imaging by Nuclear Magnetic Resonance*, 5 Magnetic Resonance Quarterly 263 (1989). The contents of these documents are hereby incorporated by reference as if recited in full herein.

In particular embodiments, the present invention can be practiced to give a quantitative assessment of perfusion as will be appreciated by one of skill in the art. According to this embodiment, signal intensity can be followed over time as noted above. Examples of such quantitative relationships were developed for use with radioactive contrast agents with MR imaging and spectroscopy methods may be particularly suitable for dissolved phase $^{129}$Xe analysis of blood vessels. See, generally, Lassen, *Cerebral Transit of an Intravascular Tracer may Allow Measurement of regional Blood Volume but not Regional Blood Flow*, 4 J. Cereb. Blood Flow and Metab. 633 (1984).

Furthermore, the inventive methods may be used for wide range of diagnostic and evaluative applications, as described herein.

Other applications of the present invention include, but are not limited to: identification and assessment of the presence or absence and/or severity of cardiac ischemias and/or infarcts; localization and assessment of thrombi and plaques; determination of "therapeutic windows" for administering heparin, vasodilators, antihypertensive agents, calcium antagonists and the like, e.g., in reversible focal ischemia; monitoring of other induced vasodilator effects; detection and quantitative evaluation of the severity of ischemias; monitoring the vasodilatory or vasocontractory effects of a physiologically active substance; and monitoring surgically induced blood perfusion variations.

The present invention may further be employed for: assessment of cerebral perfusion in following induced subarachnoid hemorrhage or in conditions marked by brain dysfunction, e.g., in connection with acute severe symptomatic hyponatremia; evaluation of new therapies, e.g., in the treatment of cerebral vasospasm (including but not limited to, anti-thrombolytic therapies, calcium channel blockers, anti-inflammatory therapies, angioplasty, and the like); assessment of the presence or absence and/or severity of ischemia in large tissue masses; assessment of the relationship between blood metabolites and cerebral perfusion in cerebral ischemia associated with acute liver failure, e.g., for the treatment of Alzheimer's disease; evaluation of new therapies for stroke, including but not limited to, t-PA, aspirin antiphospholipids, lupus anticoagulants, antiphospholipid antibodies, and the like; evaluation of risk factors for stroke, e.g., serum lipid levels; evaluation of induced brain hypothermia on cerebral perfusion during neurosurgery, e.g., for stroke; evaluation of the effects of age on cerebral perfusion, e.g., to study lacunar infarcts; and assessment of narcotics, e.g., cocaine, amphetamines, ethanol, and the like, on the ischemic brain.

Many researchers have investigated characteristic chemical shifts observed when hyperpolarized $^{129}$Xe comes into contact with different tissues, as seen in Table 1. As shown, large frequency shifts (on the order of 200 parts per million or "ppm") from free gas phase (referenced at 0 ppm) have been observed. This frequency shift is far greater than that observed with proton spectroscopy (generally stated, at most about 5 ppm). Therefore, spectroscopy is a modality which may be particularly suited to capitalize upon the behavior of hyperpolarized $^{129}$Xe.

TABLE 1

Characteristic shifts from free gaseous hyperpolarized $^{129}$Xe (referenced at 0 ppm) of hyperpolarized $^{129}$Xe when exposed to different tissues.

| Tissue | ppm | Reference |
| --- | --- | --- |
| Water | 191.2 | Wilson 99 |
| Epicardial fat | 192 | Swanson 99 |
| Brain, lipid rich | 194 | Albert 99 |
| Brain tissue | 194.5 | Swanson 97 |
| Plasma | 195.6 | Wilson 99 |
| Brain | 198.0 | Wilson 99 |
| Lung parenchyma | 198.6 | Wilson 99 |
| Brain tissue | 199 | Swanson 99 |
| Kidney | 199.8 | Wilson 99 |
| Brain—lipid poor | 201 | Albert 99 |
| Liver | 201.8 | Wilson 99 |
| T. Californica membrane | 209 | Miller 81 |
| RBC (oxygenated) | 213.0 | Wilson 99 |
| RBC (de-oxygenated) | 216.0 | Albert 99 |

As discussed hereinabove, hyperpolarized $^{129}$Xe can be administered to a patient by inhalation or injection. If the administration modality is injection, $^{129}$Xe can be suspended in a carrier fluid or injected directly such as in gaseous form. However, regardless of what tissue is of interest, if the $^{129}$Xe is suspended in a carrier fluid, it is likely that the carrier fluid itself distorts the results of the spectra and/or substantially obscures a spectral peak of interest. The carrier fluid may also react with the target tissue (region of interest) and/or potentially produce compounds with molecules in or around the tissue of interest, which may thereby cause the chemical shift of hyperpolarized $^{129}$Xe to differ from that which would be observed with merely the tissue of interest and hyperpolarized $^{129}$Xe. Therefore, direct injection of gaseous $^{129}$Xe or administration via inhalation may be particularly suitable for certain embodiments or applications. For additional discussion of direct injection of gaseous $^{129}$Xe, see co-pending U.S. application Ser. No. 09/804,369, the contents of which are hereby incorporated by reference as if recited in full herein.

In certain embodiments, the spectral peaks may be quantified by normalizing the spectral data. The term "normalizing" means to adjust the signal data of the spectral peak or peaks of interest to account for selected signal variables. This adjustment may include using the mathematic ratio of the values of certain peaks associated with selected known biomatter (RBC, plasma, etc) within the response spectrum to quantify the hyperpolarized gas signal in the region of interest. The adjustment may include using the polarization level (and/or quantity) of the administered gas measured at the time of delivery to obtain a base or reference spectrum to quantify the magnitude of the signal. As such, the normalization can use relative data and/or absolute data. For example, the ratio of the spectra for the blood to spectra of the brain tissue (the ratio of the magnitude or area of selected spectral peaks) can be calculated. Of course, other known chemical shift peak locations can also be used to normalize the value of the spectra peak of interest. The absolute data can include data associated with the polarization level of the gas as it is delivered to the patient and/or the amount of gas administered thereto (to account for signal strength).

A region-specific NMR coil can be positioned over the region of interest and to transmit a selected RF pulse sequence. The coil receives a FID signal. Localizing gradients can also be applied about the region of interest so as to localize the resonance region. For example, localizing gradients can be applied so that a desired region of interest is excited (either the left or right). In any event, the Fourier Transform of the acquired data is then calculated. The transformed signal data can be further processed which may include, but is not limited to, one or more of subtracting background noise, filtering undesirable signal data (such as those portions of the signal or spectra attributed to carrier liquids or deposits in non-target tissue or blood and the like), determining the frequency shift and size of the shift for any number of peaks within pre-determined ranges in the spectrum, and normalizing the data such as finding the ratios between magnitudes and/or areas of different spectral peaks within the response spectrum or accounting for polarization level and amount of polarized gas delivered to the subject. For further discussion of exemplary background subtraction or adjustment methods and cardiac gating methods, see co-pending U.S. application Ser. Nos. 09/271,476 and 09/271,476 incorporated by reference herein.

The present invention finds use for both pre-clinical animal studies, veterinary and medical applications. The present invention may be advantageously employed for diagnostic evaluation and/or treatment of subjects, in particular human subjects, because it may be safer (e.g., less toxic) than other methods known in the art (e.g., radioactive methods). In general, the inventive methods may be more readily accepted because they avoid radioactivity or toxic levels of chemicals or other agents. Subjects according to the present invention can be any animal subject, and are preferably mammalian subjects (e.g., humans, canines, felines, bovines, caprines, ovines, equines, rodents, porcines, and/or lagomorphs), and more preferably are human subjects.

The present invention is described with reference to flowchart illustrations and/or block diagrams of methods, and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, embedded processor or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

As will be appreciated by one of skill in the art, the present invention may be embodied as a method, data or signal processing system, or computer program product. Accordingly, the present invention may take the form of an entirely software embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk or C++. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user=s computer and partly on a remote computer or entirely on the remote computer. In the latter scenario, the remote computer may be connected to the user=s computer through a local area network (LAN) or a wide area network (WAN), or the connection may be made to an external computer (for example, through the Internet using an Internet Service Provider).

The flowcharts and block diagrams illustrate methods to obtain dynamic NMR signal data and analyze and evaluate the data to (a) quantify the thickness of physiologic barriers such as structures or environments including tissue, membrane, or linings; (b) quantify the width of lumens or channels; (c) evaluate the adequacy of physiologic function of certain systems or membranes; (d) identify disruptions or compromised integrity of the barriers, structures, lumens, or channels and/or to identify disorders associated therewith; and (e) to provide perfusion map of the brain based on a concurrent acquisition of dynamic data at multiple chemical shifts associated with the brain across a plurality of compartments of the brain according to embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. An in vivo method for evaluating the blood brain barrier in a subject, comprising:
   delivering polarized $^{129}$Xe in vivo to a subject such that it diffuses into the blood stream and across the blood brain membrane to be taken up in tissue in the brain across the membrane, the polarized gas in the blood and brain tissue having distinct corresponding polarized gas NMR chemical shift signal frequencies;
   destroying the polarization of the polarized $^{129}$Xe in the brain tissue;
   obtaining an NMR spectroscopic signal of the polarized gas in the subject over time at the brain tissue chemical shift frequency to generate at least one dynamic data set of the NMR spectroscopic signal strength values over time;
   evaluating the dynamic data; and
   assessing the blood brain barrier based on data provided by said obtaining and evaluating steps.

2. A method according to claim 1, wherein the evaluating step evaluates the polarized gas transit behavior of the polarized gas, the gas transit time corresponds to the time it takes the polarized gas to travel across the membrane and then enter the brain tissue after said destroying step.

3. A method according to claim 2, wherein the brain tissue is gray matter, and wherein the step of assessing includes determining the thickness of the blood brain barrier.

4. A method according to claim 1, wherein the obtaining step is carried out to monitor the efficacy of a pharmaceutical agent administered to the subject to evaluate its impact on the thickness of the blood brain barrier.

5. A method according to claim 4, wherein the obtaining step is carried out both before and after the administration of the agent to the subject.

6. A method according to claim 1, wherein the step of evaluating comprises assessing perfusion and ventilated oxygen levels in gray and white matter brain tissue based on data provided by said obtaining step.

* * * * *